US010524958B2

(12) United States Patent
Camras et al.

(10) Patent No.: US 10,524,958 B2
(45) Date of Patent: Jan. 7, 2020

(54) METHOD AND APPARATUS FOR REDUCING INTRAOCULAR PRESSURE

(71) Applicant: CAMRAS VISION, INC., Research Triangle Park, NC (US)

(72) Inventors: Lucinda Camras, Durham, NC (US); Rolf Erik Ypma, Durham, NC (US)

(73) Assignee: Alievio, Inc., Research Triangle Park, NC (US)

( * ) Notice: Subject to any disclaimer, the term of this patent is extended or adjusted under 35 U.S.C. 154(b) by 656 days.

(21) Appl. No.: 14/871,095

(22) Filed: Sep. 30, 2015

(65) Prior Publication Data

US 2017/0087016 A1    Mar. 30, 2017

(51) Int. Cl.
*A61F 9/007*    (2006.01)

(52) U.S. Cl.
CPC .................. *A61F 9/00781* (2013.01)

(58) Field of Classification Search
CPC .................................................. A61F 9/00781
USPC ........ 604/7–10, 264, 30, 6.09, 6.1; 606/153, 606/108
See application file for complete search history.

(56) References Cited

U.S. PATENT DOCUMENTS

| 3,788,327 | A | | 1/1974 | Donowitz et al. |
| 4,886,488 | A | | 12/1989 | White |
| 5,041,081 | A | * | 8/1991 | Odrich ................ A61F 9/00781 604/9 |
| 5,127,901 | A | | 7/1992 | Odrich |
| 5,171,213 | A | | 12/1992 | Price, Jr. |
| 5,300,020 | A | | 4/1994 | L'Esperance, Jr. |
| 5,346,464 | A | * | 9/1994 | Camras ................ A61F 9/00781 604/294 |
| 5,626,558 | A | | 5/1997 | Suson |
| 5,656,026 | A | | 8/1997 | Joseph |

(Continued)

FOREIGN PATENT DOCUMENTS

| EP | 0102747 A1 | 3/1984 |
| EP | 2 896 386 A1 | 7/2015 |

(Continued)

OTHER PUBLICATIONS

International Search Report mailed in PCT/US17/40738 dated Nov. 2, 2017, 4 pages.

(Continued)

*Primary Examiner* — Leslie R Deak
(74) *Attorney, Agent, or Firm* — McDonell Boehnen Hulbert & Berghoff LLP

(57) ABSTRACT

An apparatus for reducing intraocular pressure is provided. A tube extends from an inlet end in fluid communication with an anterior chamber of the eye, to direct an aqueous humor flow from the anterior chamber to an outlet end in fluid communication with a cavity, defined by a housing, for receiving the aqueous humor. A proximal end of an elongate tubular member defining a longitudinally-extending channel is engaged with the housing such that the channel is in fluid communication with the cavity and such that a distal end of the tubular member is spaced apart from the housing, wherein the channel is configured to receive the aqueous humor from the cavity and to direct the aqueous humor through the distal end to a drainage site disposed distally to the anterior chamber and to the housing. An associated method is also provided.

38 Claims, 16 Drawing Sheets

(56) References Cited

U.S. PATENT DOCUMENTS

| | | | |
|---|---|---|---|
| 5,743,868 A | 4/1998 | Brown et al. | |
| 5,807,302 A | 9/1998 | Wandel | |
| 5,830,173 A | 11/1998 | Avery et al. | |
| 5,882,327 A | 3/1999 | Jacob | |
| 6,077,299 A | 6/2000 | Adelberg et al. | |
| 6,261,256 B1 | 7/2001 | Ahmed | |
| 6,537,241 B1 | 3/2003 | Odland | |
| 6,544,208 B2 | 4/2003 | Ethier et al. | |
| 6,558,342 B1 | 5/2003 | Yaron et al. | |
| 6,595,945 B2 | 7/2003 | Brown | |
| 6,881,198 B2 | 4/2005 | Brown | |
| 7,118,547 B2 | 10/2006 | Dahan | |
| 7,135,009 B2 | 11/2006 | Tu et al. | |
| 7,156,821 B2 | 1/2007 | Dohlman | |
| 7,186,233 B2 | 3/2007 | Dohlman | |
| 7,192,412 B1 | 3/2007 | Zhou et al. | |
| 7,458,953 B2 | 12/2008 | Peyman | |
| 7,641,627 B2 * | 1/2010 | Camras | A61F 9/00781 604/264 |
| 7,670,310 B2 | 3/2010 | Yaron et al. | |
| 8,579,848 B2 | 11/2013 | Field et al. | |
| 8,628,492 B2 | 1/2014 | Lin et al. | |
| 8,632,489 B1 | 1/2014 | Ahmed | |
| 8,753,305 B2 | 6/2014 | Field et al. | |
| 8,986,240 B2 | 3/2015 | Dos Santos et al. | |
| 8,998,838 B2 | 4/2015 | Yalamanchili | |
| 9,072,588 B2 | 7/2015 | Böhm et al. | |
| 9,101,445 B2 | 8/2015 | Bigler et al. | |
| 9,132,034 B2 | 9/2015 | Dos Santos | |
| 9,155,653 B2 | 10/2015 | Field | |
| 9,186,274 B2 | 11/2015 | Camras et al. | |
| 9,226,851 B2 | 1/2016 | Gunn | |
| 9,259,353 B2 | 2/2016 | Dos Santos et al. | |
| 9,333,115 B2 | 5/2016 | Dos Santos | |
| 9,339,187 B2 | 5/2016 | Rickard | |
| 9,381,301 B2 | 7/2016 | Lattanzio et al. | |
| 9,456,924 B2 | 10/2016 | Noroozi et al. | |
| 9,492,321 B2 | 11/2016 | Gunn et al. | |
| 9,572,712 B2 | 2/2017 | Gunn | |
| 9,622,910 B2 | 4/2017 | Field et al. | |
| 9,681,983 B2 | 6/2017 | Lind | |
| 2002/0143284 A1 * | 10/2002 | Tu | A61F 9/0017 604/9 |
| 2002/0169468 A1 | 11/2002 | Brown | |
| 2004/0073156 A1 * | 4/2004 | Brown | A61F 9/00781 604/8 |
| 2004/0127843 A1 | 7/2004 | Tu et al. | |
| 2004/0215126 A1 | 10/2004 | Ahmed | |
| 2004/0249441 A1 | 12/2004 | Miller et al. | |
| 2004/0254521 A1 | 12/2004 | Simon | |
| 2005/0049578 A1 | 3/2005 | Tu et al. | |
| 2005/0119737 A1 | 6/2005 | Bene et al. | |
| 2005/0240142 A1 | 10/2005 | Dohlman | |
| 2005/0240143 A1 | 10/2005 | Dohlman | |
| 2006/0036207 A1 | 2/2006 | Koonmen et al. | |
| 2006/0069340 A1 | 3/2006 | Simon | |
| 2006/0116626 A1 | 6/2006 | Smedley et al. | |
| 2006/0189915 A1 | 8/2006 | Camras | |
| 2006/0235367 A1 | 10/2006 | Takashima et al. | |
| 2007/0004998 A1 | 1/2007 | Rodgers et al. | |
| 2007/0156079 A1 | 7/2007 | Brown | |
| 2007/0254005 A1 | 11/2007 | Pathak et al. | |
| 2008/0228127 A1 | 9/2008 | Burns et al. | |
| 2009/0036818 A1 | 2/2009 | Grahn et al. | |
| 2009/0117166 A1 | 5/2009 | Myung et al. | |
| 2009/0326432 A1 | 12/2009 | Schmidt et al. | |
| 2010/0056979 A1 | 3/2010 | Smedley et al. | |
| 2010/0057055 A1 | 3/2010 | Camras et al. | |
| 2010/0114006 A1 | 5/2010 | Baerveldt | |
| 2011/0071456 A1 | 3/2011 | Rickard | |
| 2011/0105986 A1 | 5/2011 | Bronstein et al. | |
| 2012/0302861 A1 | 11/2012 | Marshall et al. | |
| 2013/0096483 A1 | 4/2013 | Dacquay | |
| 2013/0150775 A1 | 6/2013 | Dos Santos et al. | |
| 2013/0150776 A1 | 6/2013 | Böhm et al. | |
| 2013/0150777 A1 | 6/2013 | Böhm et al. | |
| 2013/0150778 A1 | 6/2013 | Dos Santos | |
| 2013/0150779 A1 | 6/2013 | Field | |
| 2013/0218064 A1 | 8/2013 | Rickard | |
| 2013/0317412 A1 | 11/2013 | Dacquay et al. | |
| 2013/0317413 A1 | 11/2013 | Field et al. | |
| 2014/0005587 A1 | 1/2014 | Gelvin et al. | |
| 2014/0066832 A1 | 3/2014 | Ovchinnikov et al. | |
| 2014/0081195 A1 | 3/2014 | Clauson | |
| 2014/0163448 A1 | 6/2014 | Lind et al. | |
| 2014/0171777 A1 | 6/2014 | Sanchez et al. | |
| 2015/0045716 A1 | 2/2015 | Gallardo Inzunza | |
| 2015/0057595 A1 | 2/2015 | Gunn et al. | |
| 2015/0057596 A1 | 2/2015 | Lind et al. | |
| 2015/0057597 A1 | 2/2015 | Johnson et al. | |
| 2015/0202082 A1 | 7/2015 | Ilios et al. | |
| 2015/0230983 A1 | 8/2015 | Johnson | |
| 2015/0230984 A1 | 8/2015 | Gunn | |
| 2015/0257931 A1 | 9/2015 | Sanchez et al. | |
| 2015/0265469 A1 | 9/2015 | Olson et al. | |
| 2016/0058615 A1 | 3/2016 | Camras et al. | |
| 2016/0058616 A1 | 3/2016 | Camras et al. | |
| 2016/0067092 A1 | 3/2016 | Lind et al. | |
| 2016/0235298 A1 | 8/2016 | Gunn | |
| 2016/0242962 A1 | 8/2016 | Torello et al. | |
| 2016/0296371 A1 | 10/2016 | Gelvin | |
| 2017/0348148 A1 | 12/2017 | Bigler et al. | |
| 2017/0348149 A1 | 12/2017 | Stergiopulos et al. | |
| 2018/0078416 A1 | 3/2018 | Christiansen | |
| 2018/0092774 A1 | 4/2018 | Mehta | |

FOREIGN PATENT DOCUMENTS

| | | |
|---|---|---|
| WO | 00/64393 A1 | 11/2000 |
| WO | 2009/105573 A1 | 8/2009 |
| WO | 2013/155252 A1 | 10/2013 |
| WO | 2014/036437 A1 | 3/2014 |
| WO | 2014/130574 A1 | 8/2014 |
| WO | WO 2016/033270 A1 | 3/2016 |
| WO | 2016/100500 A1 | 6/2016 |
| WO | 2017/059272 A1 | 4/2017 |
| WO | 2017/106517 A1 | 6/2017 |
| WO | 2018/009556 A1 | 1/2018 |

OTHER PUBLICATIONS

International Search Report mailed in PCT/US16/054828 dated Dec. 13, 2016, 1 page.

International Search Report and Written Opinion mailed in PCT/US18/029717 dated Sep. 21, 2018, 20 pages.

Dohlman et al., "Shunts to Divert Aqueous Humor to Distant Epithelialized Cavities After Keratoprosthesis Surgery", Glaucoma, 2010, 19(2), 111-115.

Molteno et al., "Otago Glaucoma Surgery Outcome Study: Factors Controlling Capsule Fibrosis around Molteno Implants with Histopathological Correlation", The American Academy of Opthalmology, 2003, 110(11), 2198-2206.

* cited by examiner

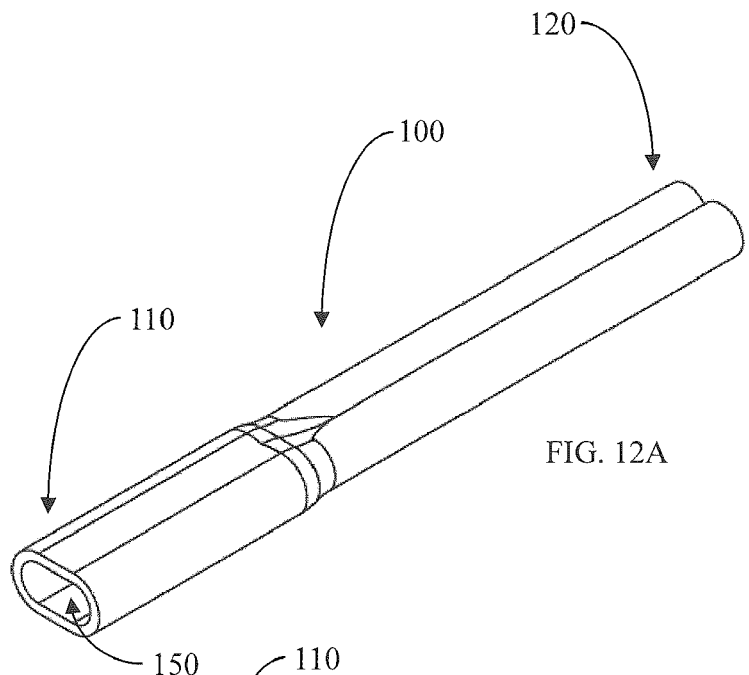
FIG. 12A
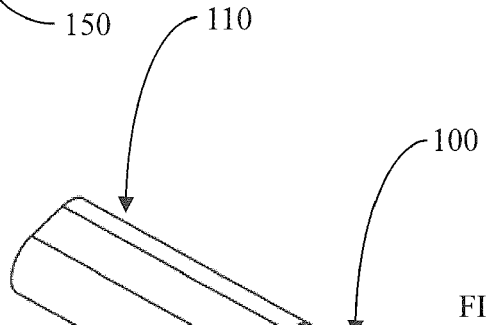
FIG. 12B
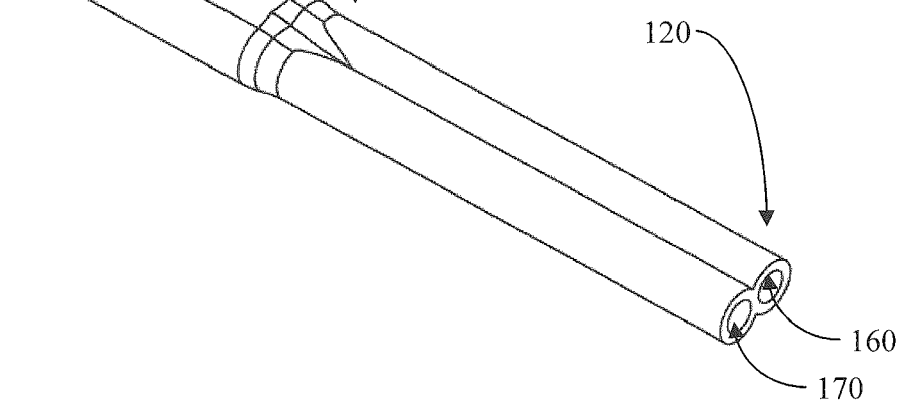

METHOD AND APPARATUS FOR REDUCING INTRAOCULAR PRESSURE

BACKGROUND

Field of the Disclosure

Aspects of the present disclosure are generally directed to an apparatus and method for draining aqueous humor from an anterior chamber of an eye to a location external or distal to the anterior chamber for reducing intraocular pressure and, more particularly, to an implantable apparatus for regulating intraocular pressure by directing a flow of the aqueous humor externally from the anterior chamber of the eye to an external or distal drainage site for reducing and regulating intraocular pressure.

Description of Related Art

Glaucoma is a group of chronic optic nerve diseases and a leading cause of irreversible blindness. The major risk factor in glaucoma is elevated intraocular pressure due to improper drainage of aqueous humor from the eye. Reduction of intraocular pressure is the only proven treatment to stop the progression of vision loss.

Standard glaucoma surgeries to reduce intraocular pressure, such as trabeculectomies and glaucoma drainage device implantation, tend to be lengthy and traumatic with unpredictable outcomes and complication rates of 20-60%. Implantable drainage devices function to drain excess aqueous humor from the eye, and installation of such a drainage device typically requires a surgical opening made in the sclera to reach the interior of the eye, in particular the anterior chamber or the posterior chamber. Some drainage devices may then be inserted into the interior of the eye for conducting the aqueous humor to the subconjunctival space (with such a device herein referred to as a subconjunctival shunt). In some instances, the aqueous humor may then be drained from the anterior chamber externally to the conjunctiva (with such a device herein referred to as an external shunt). However, there does not appear to be any commercially available externally-applied shunts.

A problem associated with subconjunctival shunts is potential scarring of the bleb in the subconjunctival space affecting its fibrous capsule formation around the outlet, which in many cases requires surgical revision that leads to additional risk of complications. Therefore, there is an ongoing search to identify and utilize alternate drainage sites to avoid many problems associated with bleb and fibrous capsule formations.

External shunts avoid bleb and fibrous capsule formation and the unpredictability of wound healing in the subconjunctival space. However, the outlet of an external shunt may be perceived by the patient as a foreign body, especially those that lie on the corneal surface. These shunts can also be displaced by local tissue motion or extruded by constrictive wound healing processes. In addition, external shunts can expose a mechanical conduit available to transmit microorganisms from the outside to the interior of the eye, potentially leading to retrograde infection.

All drainage devices implanted in the eye have the potential to clog from proteins or other substances in the aqueous humor. Clogging reduces permeability of the device and may lead to elevation of intraocular pressure compared to baseline. Moreover, the intraocular pressure may naturally vary or fluctuate due to changes in aqueous humor dynamics of the particular eye, regardless of the effect of a drainage device.

For the foregoing reasons there is a need for an improved drainage device for directing aqueous humor away from the anterior chamber of an eye for reducing and managing intraocular pressure.

SUMMARY OF THE INVENTION

The above and other needs are met by aspects of the present disclosure which, in one aspect, provides an apparatus for draining aqueous humor from an eye for reducing intraocular pressure, wherein the eye includes an anterior chamber, a cornea, a surrounding marginal limbus by which the cornea is continuous with a scleral layer and a conjunctival layer, and an external ocular surface of the eye under an eyelid. Such an apparatus may comprise a tube extending between an inlet end and an outlet end, with the inlet end being adapted to be in fluid communication with the anterior chamber of the eye, and with the tube being adapted to direct a flow of aqueous humor from the anterior chamber and through the inlet end to the outlet end. A housing defines a cavity in fluid communication with the outlet end of the tube, wherein the cavity is configured to receive the aqueous humor. An elongate tubular member has opposed proximal and distal ends and defines a longitudinally-extending channel. The proximal end of the tubular member is engaged with the housing such that the channel is in fluid communication with the cavity and such that the distal end is spaced apart from the housing, wherein the channel is configured to receive the aqueous humor from the cavity and to direct the aqueous humor through the distal end to a drainage site disposed distally to the anterior chamber and to the housing.

Another aspect of the disclosure provides a method of manufacturing an apparatus for draining aqueous humor from an eye for reducing intraocular pressure, wherein the eye includes an anterior chamber, a cornea, a surrounding marginal limbus by which the cornea is continuous with a scleral layer and a conjunctival layer, and an external ocular surface of the eye under an eyelid. Such a method comprises engaging an outlet end of a tube into fluid communication with a cavity defined by a housing, with the outlet end extending to an inlet end adapted to be in fluid communication with the anterior chamber of the eye, and with the tube being adapted to direct the flow of aqueous humor from the anterior chamber and through the inlet end and to the outlet end such that the aqueous humor is received by the cavity. A proximal end of an elongate tubular member is engaged with the housing, wherein the tubular member has a distal end opposing the proximal end and defines a longitudinally-extending channel, such that the channel is in fluid communication with the cavity and such that the distal end is spaced apart from the housing. The channel is configured to receive the aqueous humor from the cavity and to direct the aqueous humor through the distal end to a drainage site disposed distally to the anterior chamber and to the housing.

Further features and advantages of the present disclosure are set forth in more detail in the following description.

DESCRIPTION OF THE DRAWINGS

Figure 1:
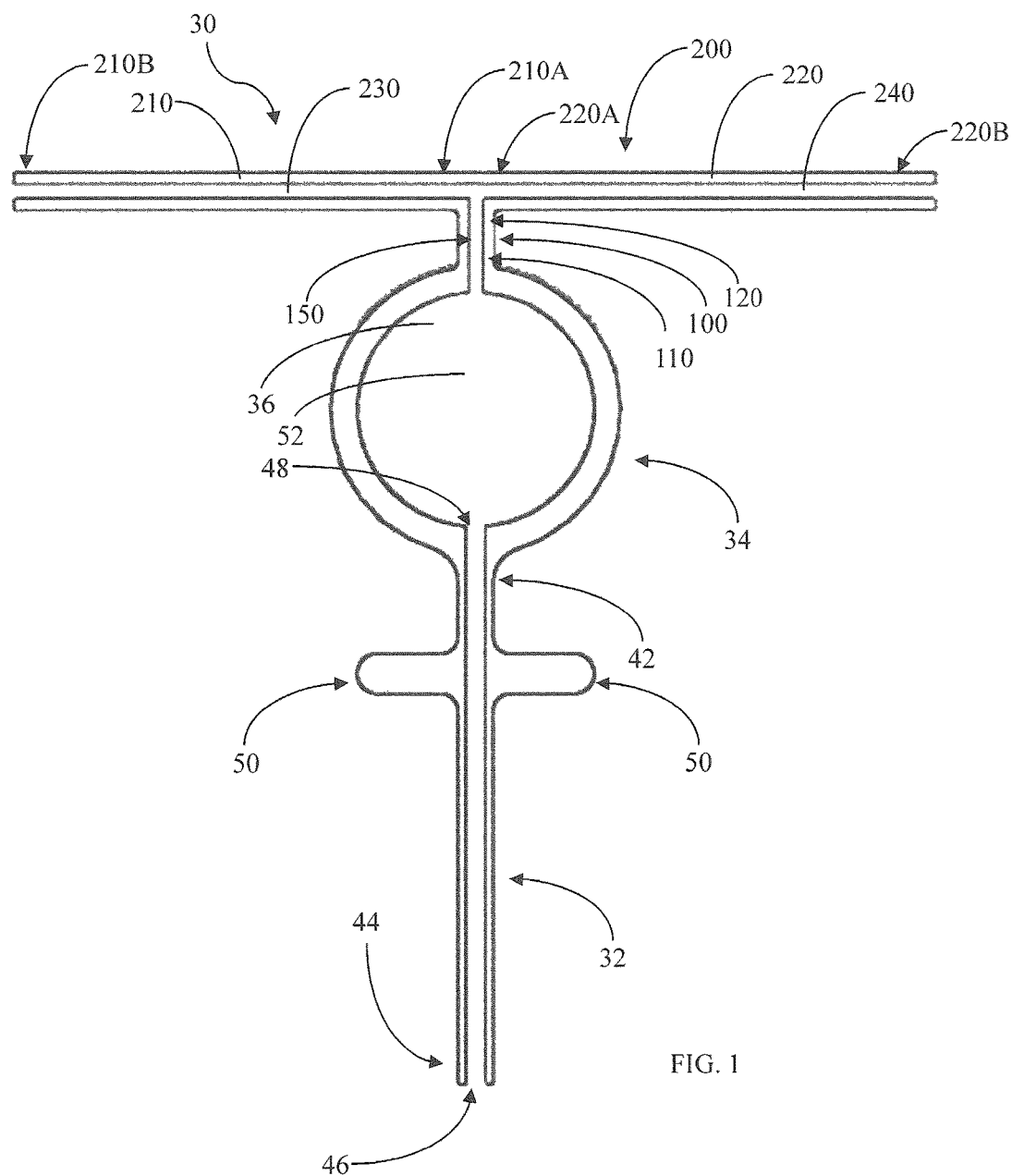
Figure 2A:
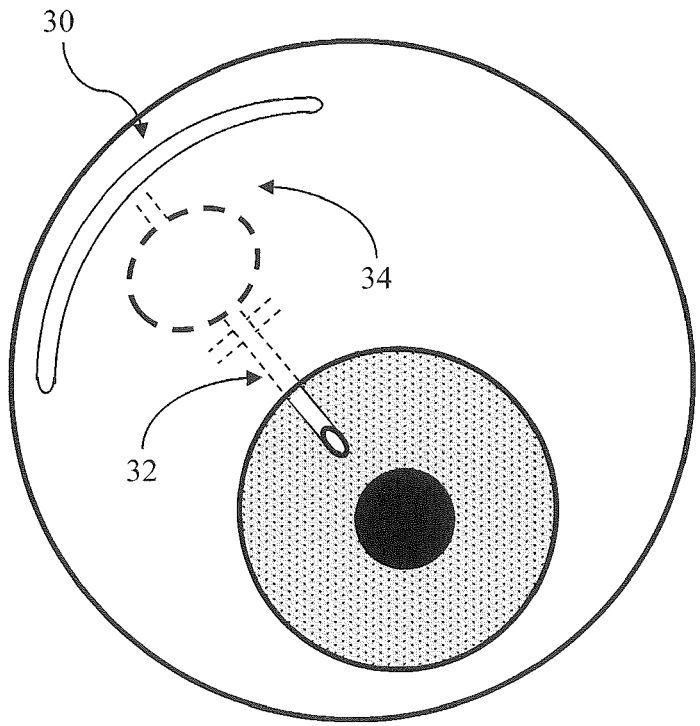
Figure 2B:
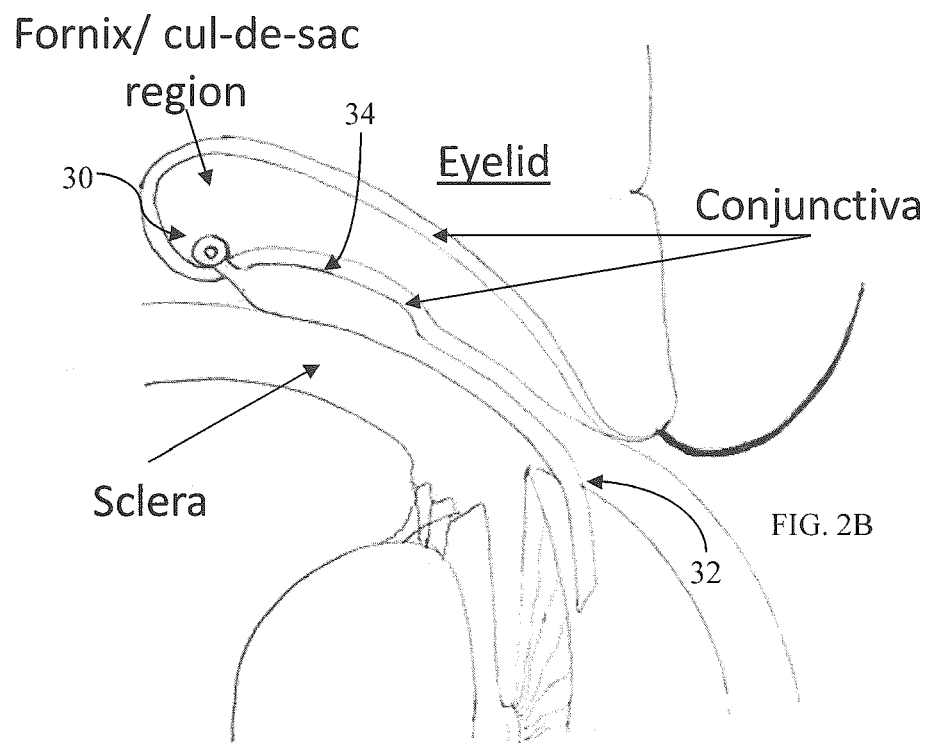
Figure 3:
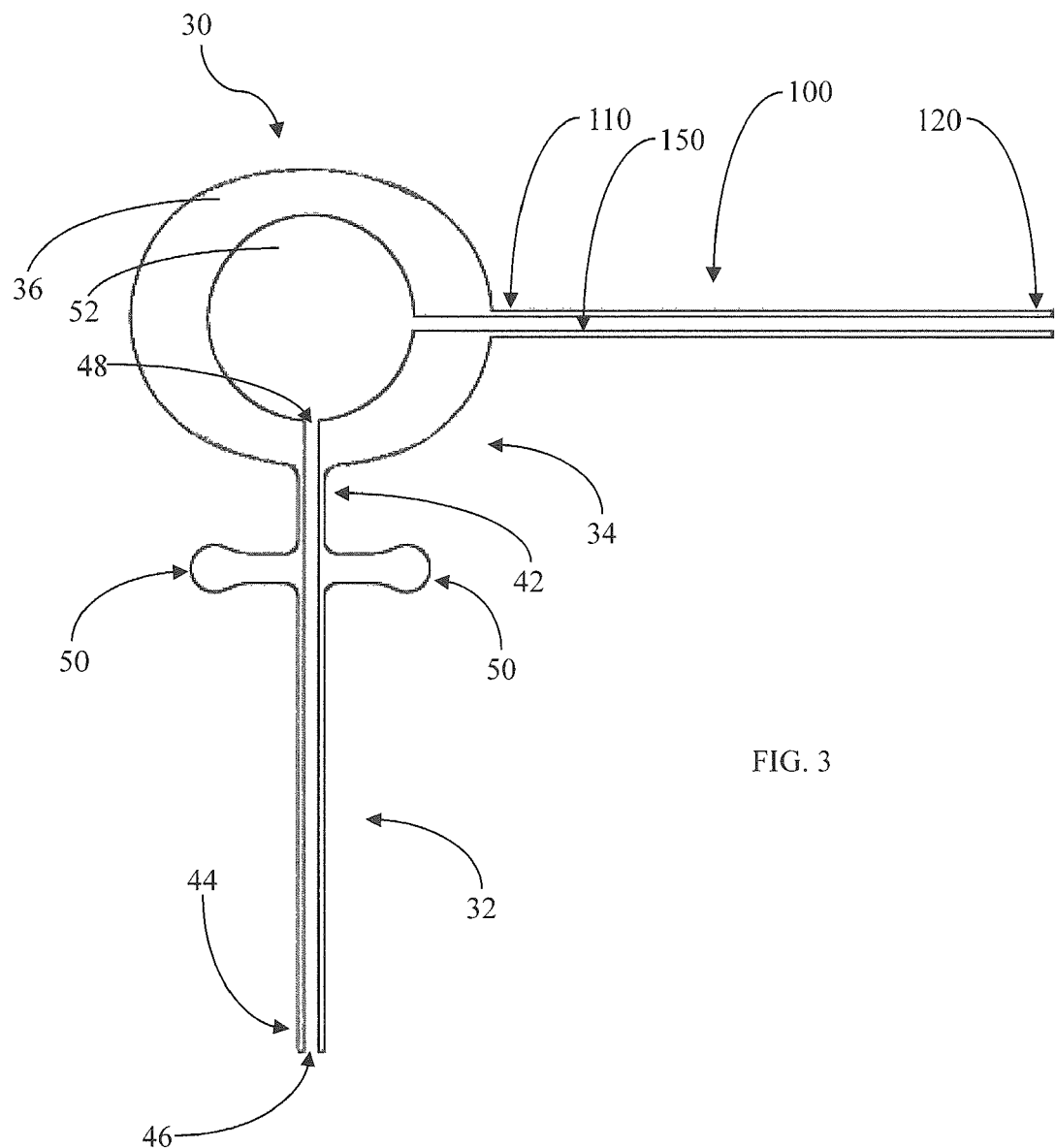
Figure 4:
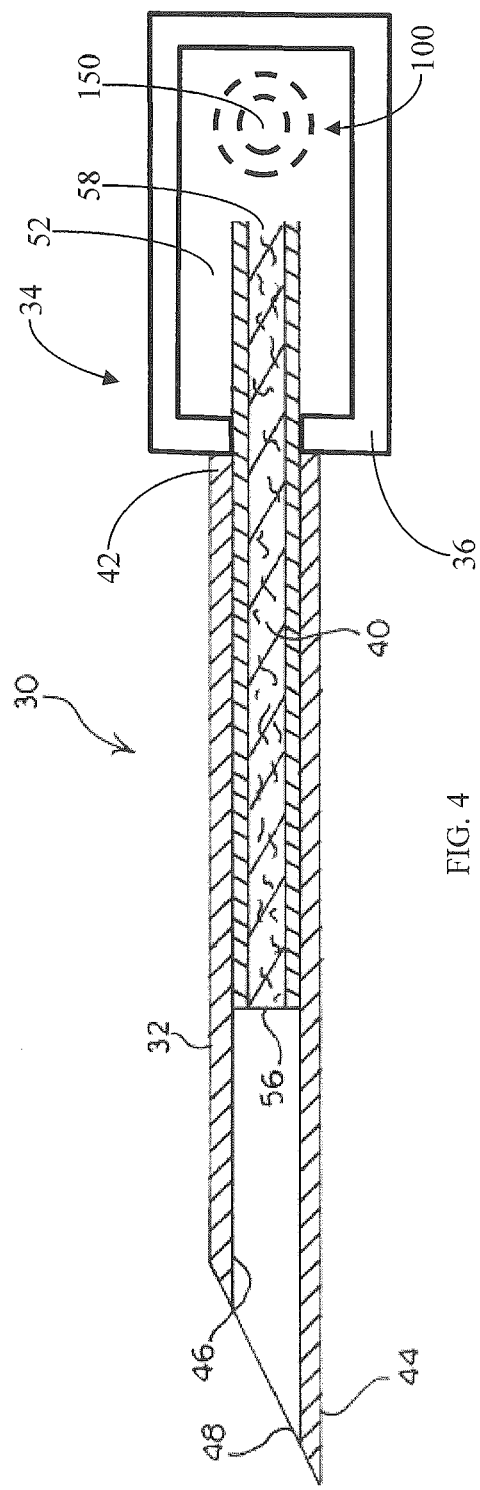
Figure 5A:
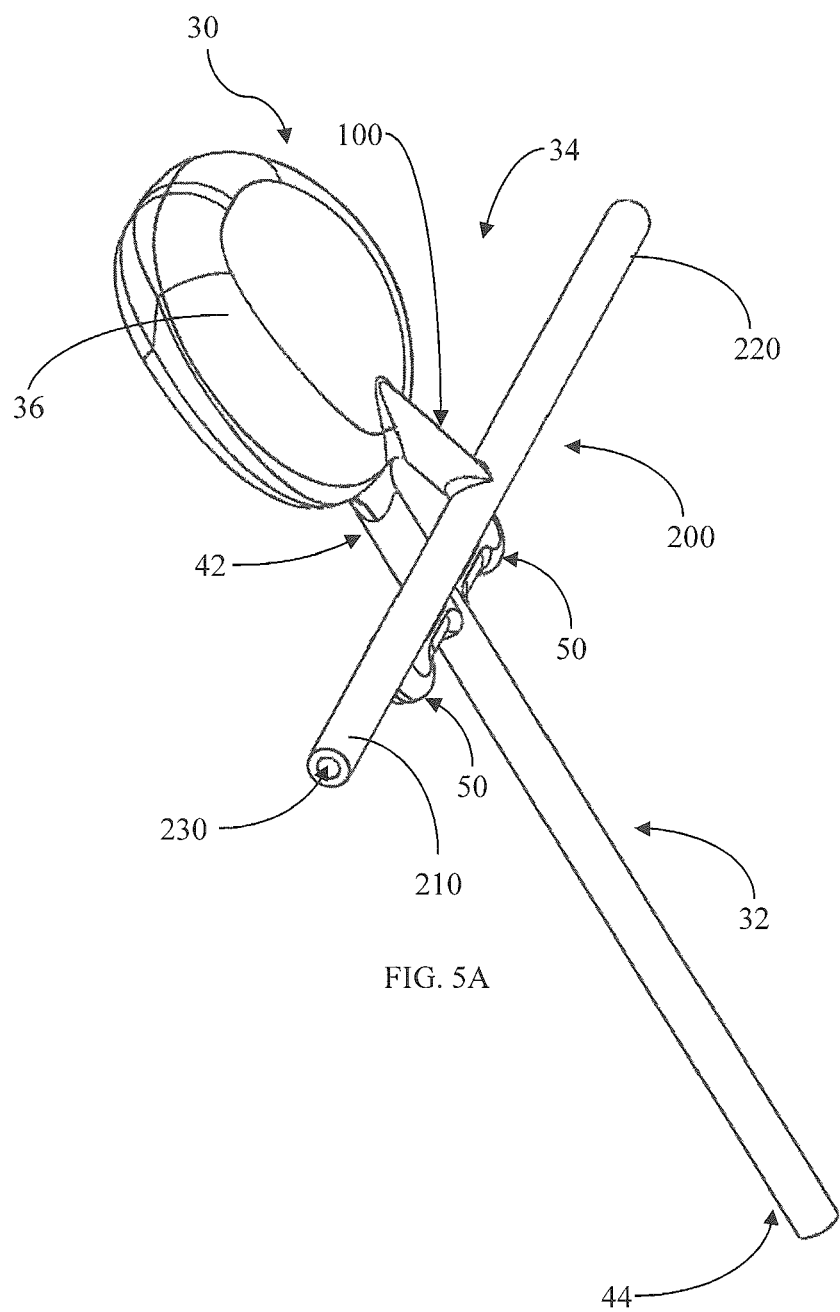
Figure 5B:
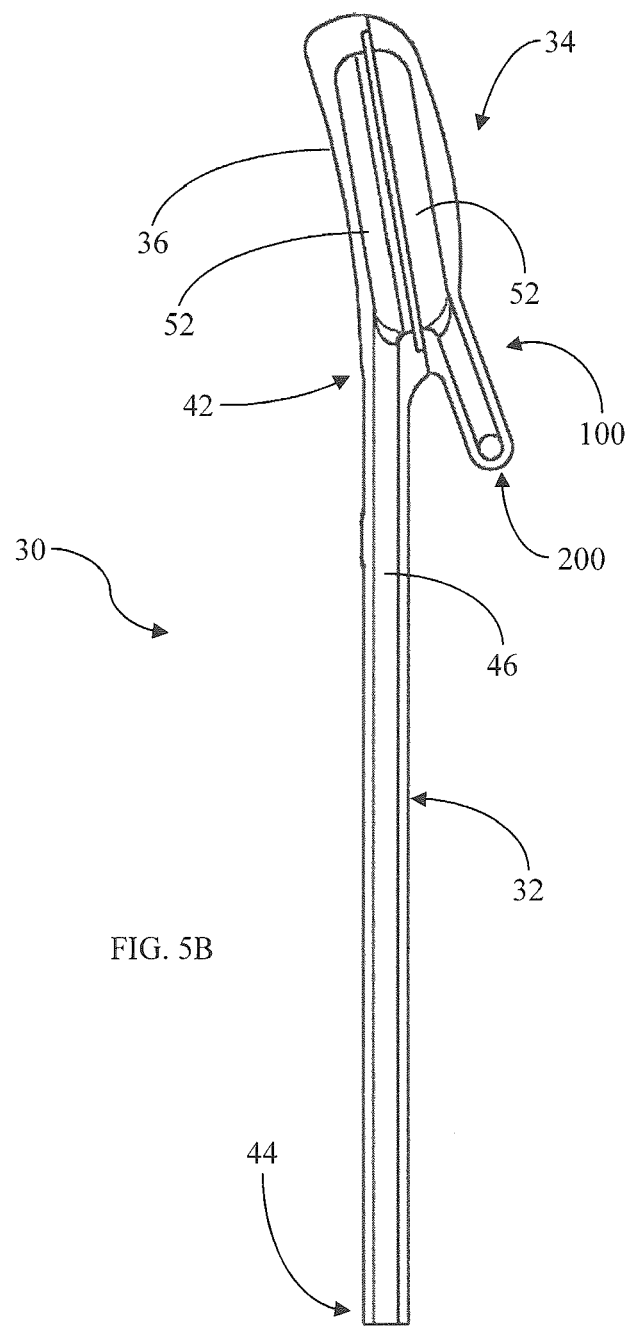
Figure 5C:
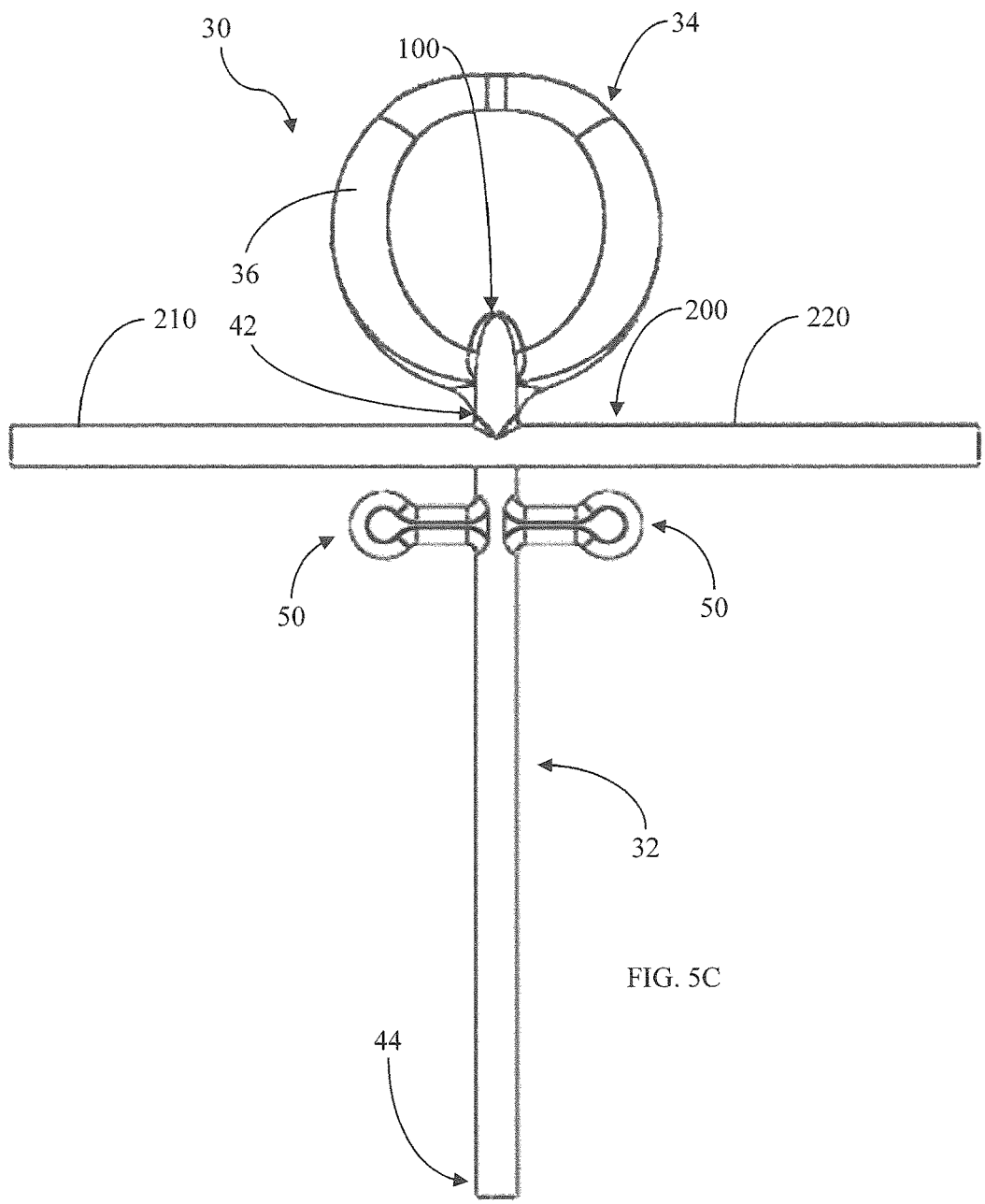
Figure 6:
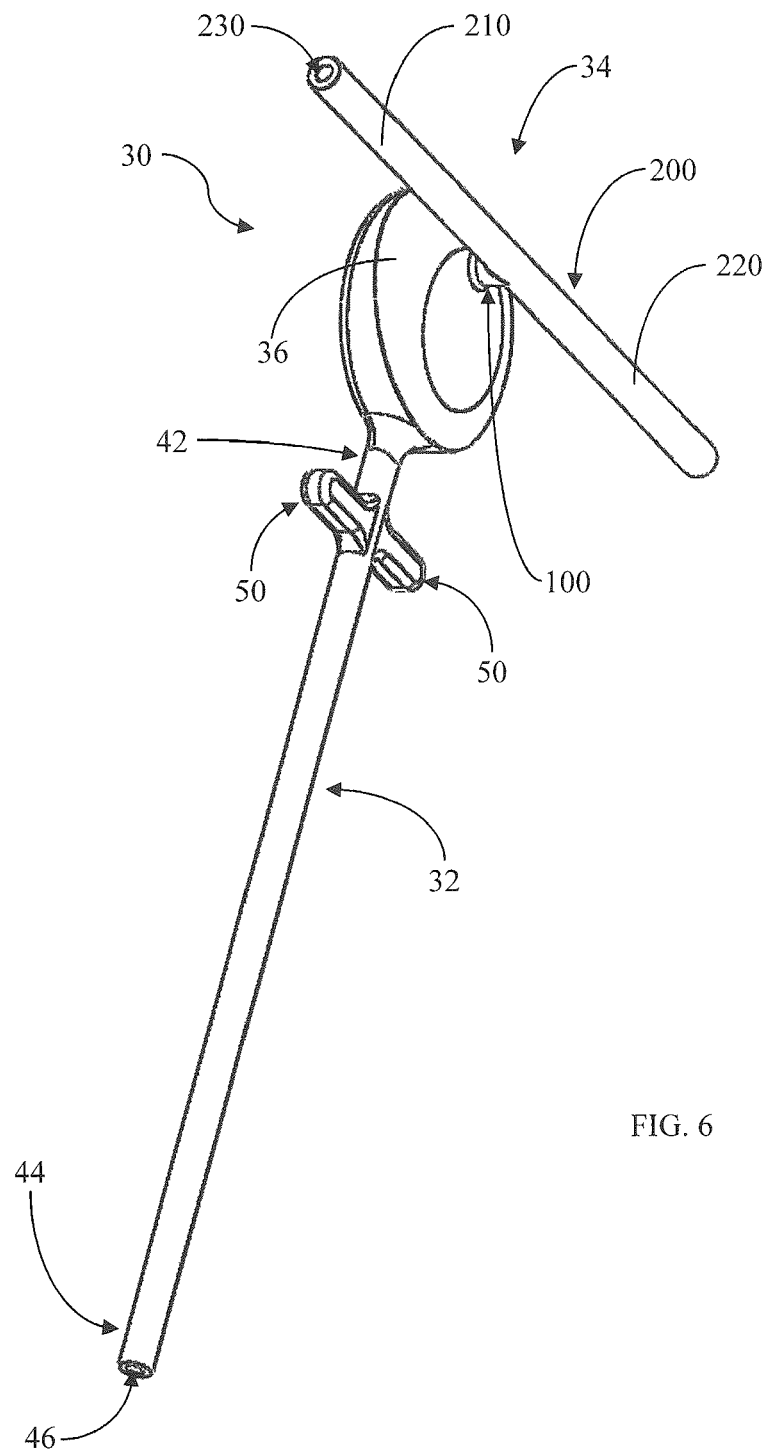
Figure 7:
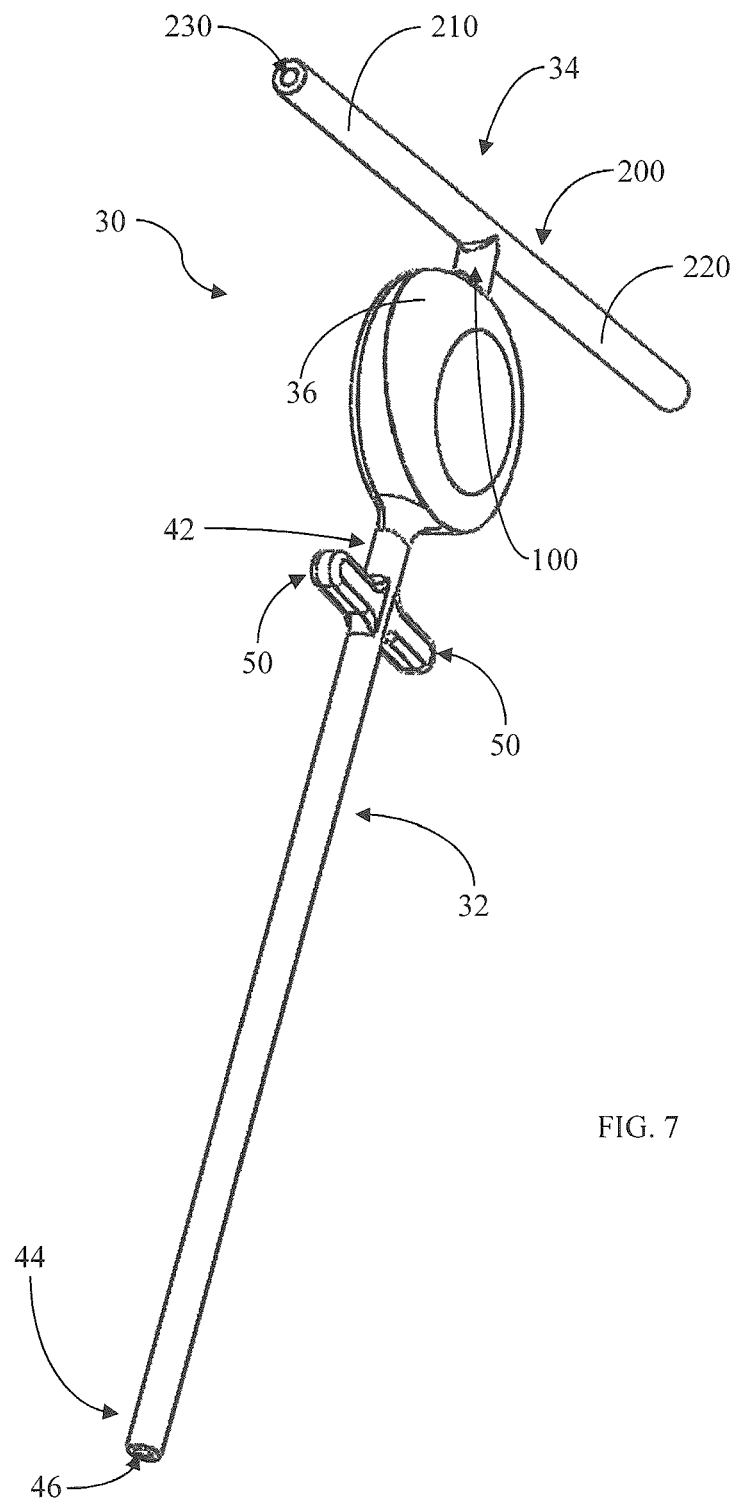
Figure 8:
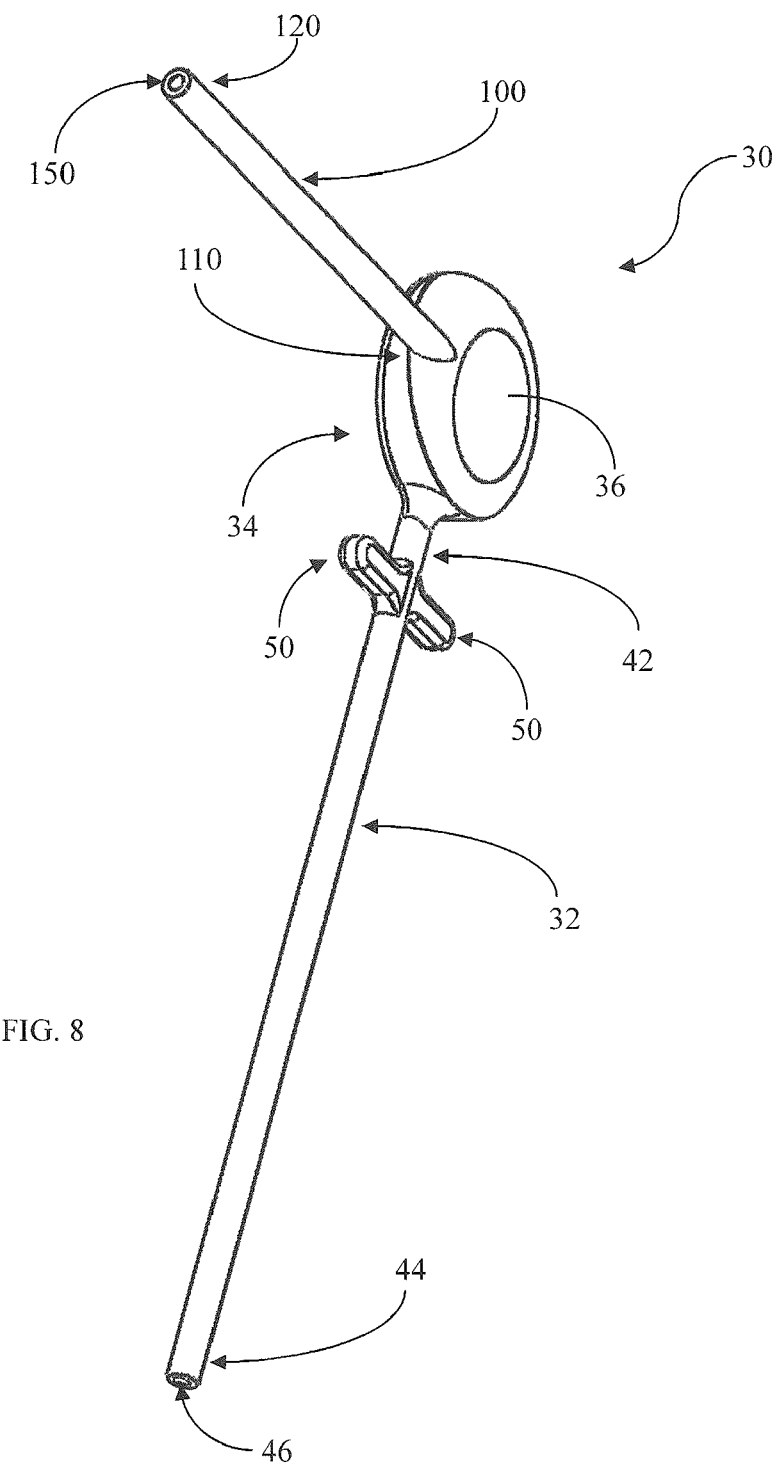
Figure 9:
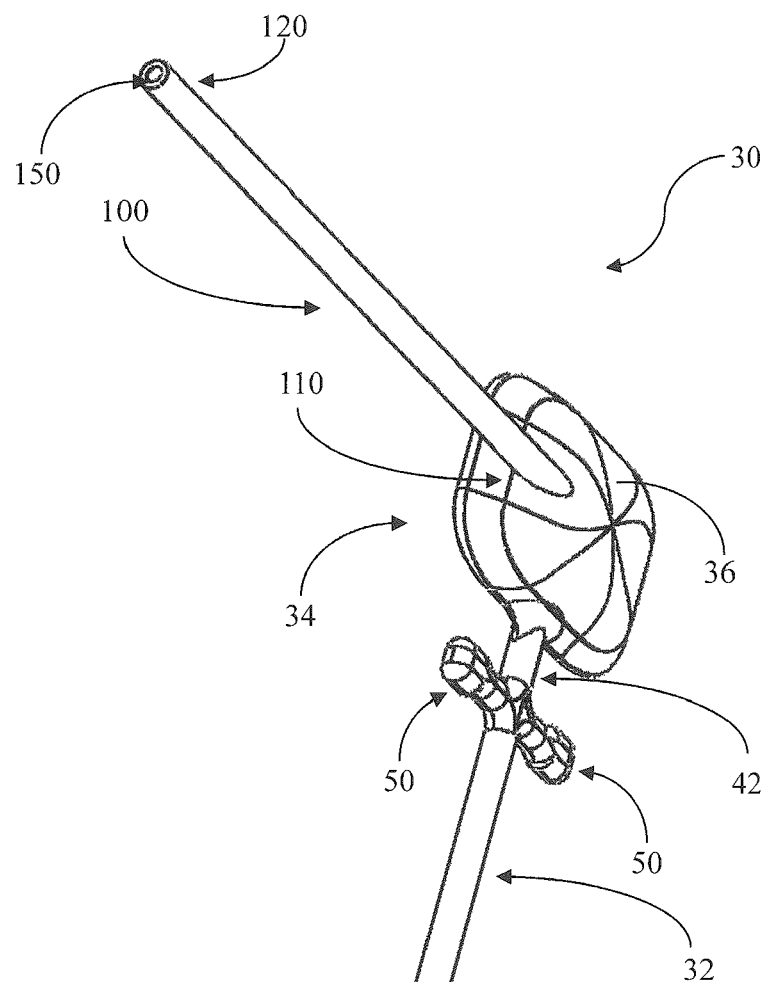
Figure 10:
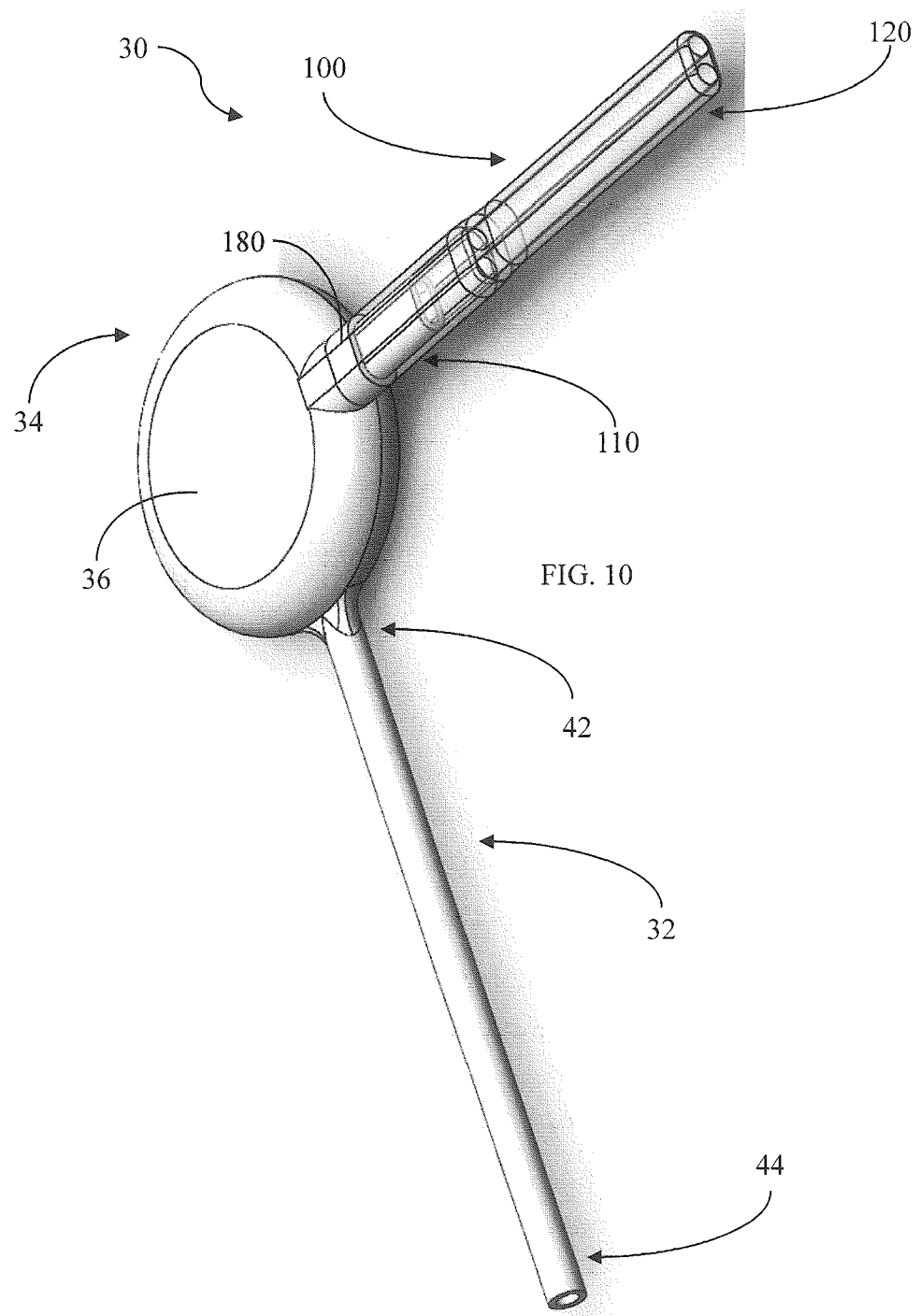
Figure 11A:
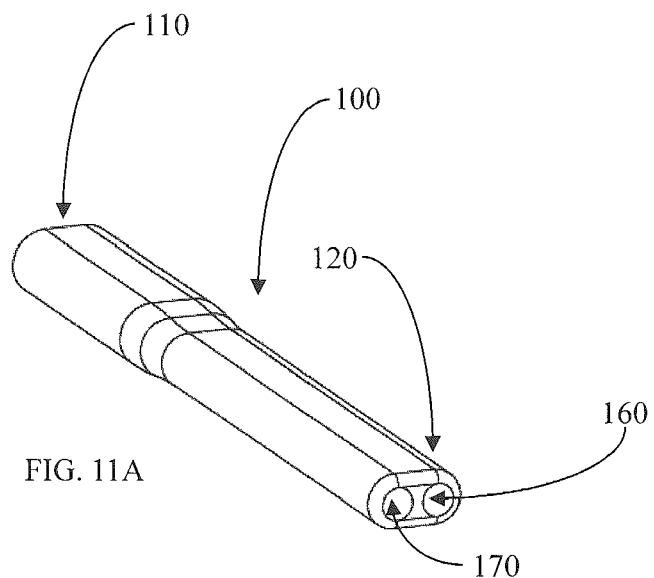
Figure 11B:
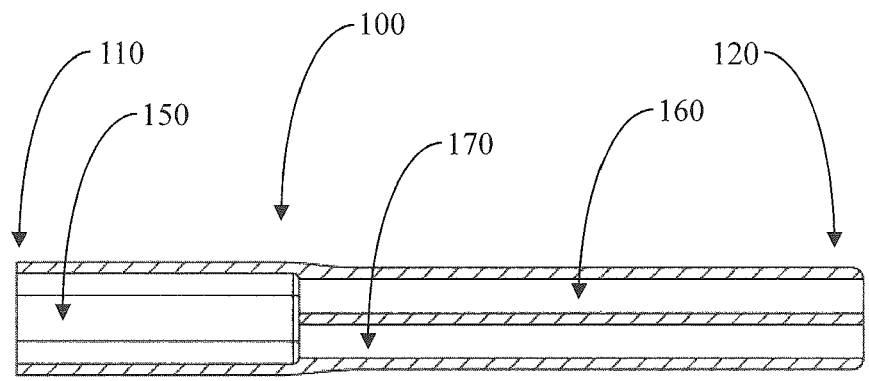
Figure 13A:
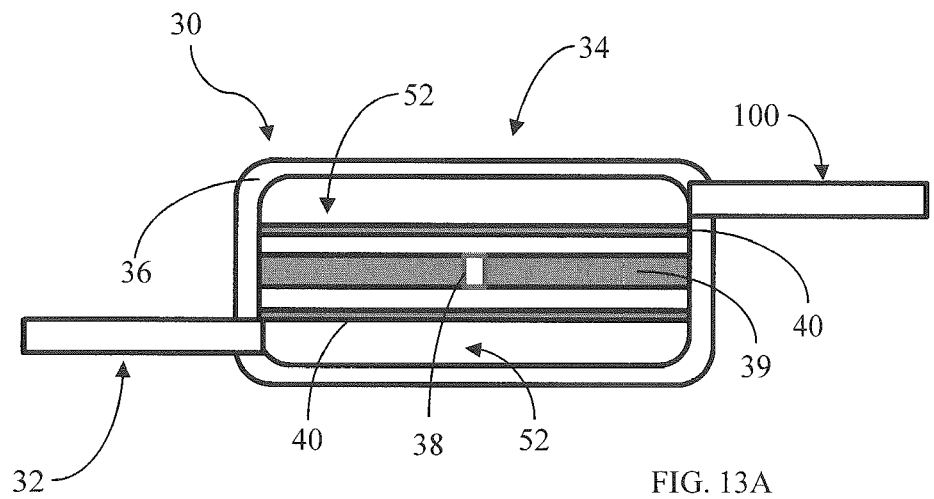
Figure 13B:
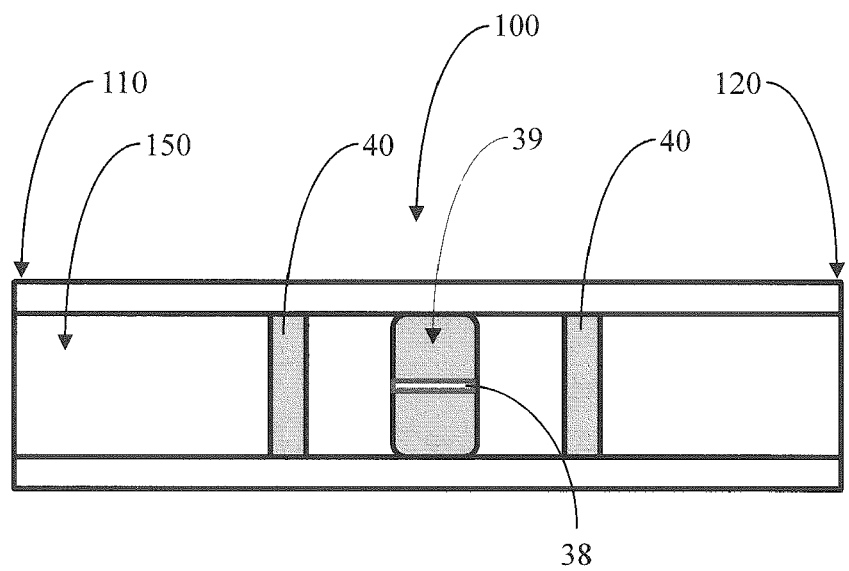
Figure 14:
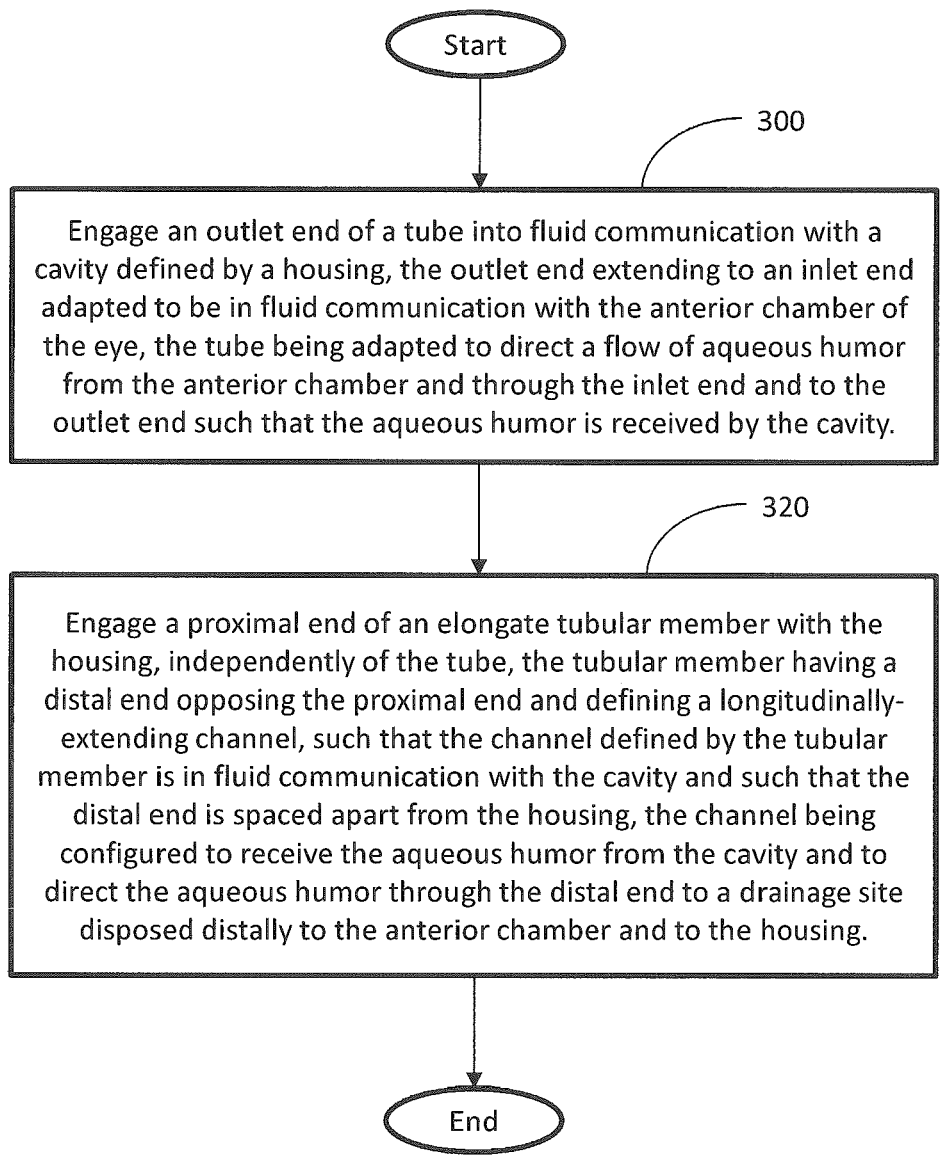

Having thus described the disclosure in general terms, reference will now be made to the accompanying drawings, which are not necessarily drawn to scale, and wherein:

FIG. 1 schematically illustrates a drainage device for reducing intraocular pressure, according to one aspect of the disclosure;

FIGS. 2A and 2B schematically illustrate an exemplary drainage device implanted in an eye, according to one aspect of the disclosure;

FIG. 3 schematically illustrates a drainage device, according to another aspect of the present disclosure;

FIG. 4 schematically illustrates a cross-sectional view of a drainage device, according to one aspect of the disclosure;

FIGS. 5A-5C schematically illustrates various views of a drainage device, according to another aspect of the disclosure;

FIGS. 6-10 schematically illustrate a drainage device, according to various embodiments of the present disclosure;

FIGS. 11A and 11B schematically illustrate an outlet tubular member for a drainage device as shown in FIG. 10, according to one embodiment of the present disclosure;

FIGS. 12A and 12B schematically illustrate an outlet tubular member for a drainage device as shown in FIG. 10, according to another embodiment of the present disclosure;

FIG. 13A schematically illustrates a cross-sectional view of a flow resistance arrangement housed in a housing of a drainage device, according to one embodiment of the present disclosure;

FIG. 13B schematically illustrates a cross-sectional view of a flow resistance arrangement housed in a outlet tubular member of a drainage device, according to one embodiment of the present disclosure; and FIG. 14 schematically illustrates a method of manufacturing a drainage device, according to one aspect of the present disclosure.

DESCRIPTION OF THE PREFERRED EMBODIMENTS

The present disclosure now will be described more fully hereinafter with reference to the accompanying drawings, in which some, but not all aspects of the disclosure are shown. Indeed, the disclosure may be embodied in many different forms and should not be construed as limited to the aspects set forth herein; rather, these aspects are provided so that this disclosure will satisfy applicable legal requirements. Like numbers refer to like elements throughout.

Certain terminology is used herein for convenience only and is not to be taken as a limitation on the scope of the disclosure. For example, words such as "upper," "lower," "left," "right," "horizontal," "vertical," "upward," and "downward" merely describe the configuration shown in the figures. Indeed, the components may be oriented in any direction and the terminology, therefore, should be understood as encompassing such variations unless specified otherwise.

FIG. 1 schematically illustrates an implantable ocular drainage device, generally designated as element 30, according to one aspect of the present disclosure. The drainage device 30 generally comprises a tubular body 32 and an outlet assembly 34 having a head portion 36. The tubular body 32 includes an inlet end 44 and a longitudinally-opposed outlet end 42, and is configured to direct a fluid between the inlet 44 and outlet 42 ends. At least a portion of the tubular body 32 of the drainage device 30 is implantable into the anterior chamber of an eye for draining aqueous humor therefrom (see, e.g., FIGS. 2A and 2B). Representative configurations of such drainage devices of the general type disclosed herein are disclosed, for example, in U.S. Patent Application Publication No. US 2010/0057055 and U.S. Pat. No. 7,641,627, each to Camras et al., and each of which is incorporated herein by reference.

The tubular body 32 of the drainage device 30 is substantially cylindrical and hollow, and has a proximal (outlet) end 42 and a distal (inlet) end 44. The tubular body 32 defines a lumen 46 that extends between the proximal end 42 and the distal end 44 with the distal end defining at least one opening 48 communicating with the lumen 46. The at least one opening 48 is configured to provide a fluid inlet at the distal end 44 of the tubular body 32. In some aspects, the distal end 44 of the tubular body 32 may be beveled (see, e.g., FIG. 4) for facilitating entry of the distal end 44 into the anterior chamber or other portion of the eye.

The lumen 46 forms at least a portion of a flow path that permits the drainage of aqueous humor from the anterior chamber of the eye to a location or drainage site external to the anterior chamber. For example, the external location/drainage site (to the anterior chamber) may be an external ocular surface of the eye. In other instances, the external location/drainage site may include another chamber within the eye, the subconjunctival space, the suprachoroidal space, or the like. In one aspect, the tubular body 32 has a length sufficient to provide fluid communication between the anterior chamber of the eye and the fornix or cul-de-sac region under the eyelid to allow aqueous humor to flow from the anterior chamber through the lumen 46 and into the tear film associated with the eye when the drainage device 30 is implanted in or attached to the eye. For this purpose, the tubular body 32 of the drainage device 30 may have a minimum length, for example, of at least about 3 mm for the outlet assembly 34 to be positioned about the fornix or cul-de-sac region under the eyelid. In one aspect, the tubular body 32 may have a length of between about 4 mm and about 9 mm for adult humans. In other instances, the tubular body 32 may be provided in a standard length that may then be cut to size by the surgeon prior to implantation. In use, the tubular body 32 may lie substantially underneath the conjunctiva with the distal (input) end disposed in the anterior (or posterior) chamber of the eye (see, e.g., FIG. 2B). One skilled in the art will appreciate, however, that the dimensions and deployment location of the drainage device 30 may vary considerably depending on the location to which the aqueous humor drained from the anterior chamber is directed.

The transverse/lateral cross-sectional shape of the tubular body 32, in addition to circular, may be other suitable shapes such as, for example, oval, square, trapezoidal, rectangular, or any combination thereof. Regardless of shape, the cross-sectional size of the lumen 46 defined by the tubular body 32 may vary to selectively alter the fluid flow characteristics of the aqueous humor. For example, a relatively small cross-sectional size can be used to restrict the fluid flow of the aqueous humor. In one aspect, the cross-sectional dimension of the lumen 46 may range, for example, from about 0.05 mm to about 1.0 mm.

An anchoring device or arrangement, such as one or more barbs (not shown) may be provided, for example, adjacent the distal end 44 of the tubular body 32 and/or in engagement with the housing or head portion 36 of the drainage device 30. The barbs can extend from a portion of the outer surface of the tubular body 32 or from an outer surface of the housing/head portion 36, for contact with the sclera when the drainage device 30 is implanted or engaged with the eye. The barbs are adapted to engage the sclera and provide stability until biointegration of the tubular body 32 and/or the housing/head portion 36 in the subconjunctival space. The barbs may be formed as part of the tubular body 32/head portion 36 of the drainage device 30 during manufacture or may be subsequently fused or bonded to the tubular body 32/head portion 36 in an appropriate manner. In other instances, the anchoring device or arrangement may comprise one or more suture bars 50 (see, e.g., FIGS. 1 and 3) may extend outwardly of the tubular body 32, between the proximal and distal ends 42, 44 thereof, and/or outwardly of the housing/head portion 36, wherein sutures (not shown) may be engaged between the sclera and the suture bars 50 to otherwise secure the tubular body 32/housing or head portion 36/drainage device 30 to the eye.

The head portion 36 of the outlet assembly 34 defines an interior cavity 52. The head portion 36 is integral with, or attached to, the proximal (outlet) end 42 of the tubular body 32 such that the cavity 52 is in fluid communication with the lumen 46 of the tubular body 32 so as to receive a flow of the aqueous humor therefrom. In the illustrated aspects, the head portion 36 and the tubular body 32 may be formed integrally as a single unit. Alternatively, each component may be formed separately from the other and cooperate, when assembled, to define the interior cavity 52. According to some aspects, the head portion 36 may be dome-shaped (or convex) to provide a substantially continuous transition surface from along an outer surface of the head portion 36 to the surface of the eye (i.e., the convex curvature is configured to make a smooth transition to the surface of the eye), for example, in instances where the head portion is configured to lie on the conjunctiva. Such a configuration/shape of the head portion 36 may be better tolerated by the patient, if the head portion does not feel like a foreign object in the eye in relation to the eyelid. However, such a configuration may also be placed or lie subconjunctivally. One skilled in the art will also appreciate that other shapes of the head portion 36 may be suitable and appropriate for providing similar sensory perception for the user. For example, a minimally protruding, substantially flat head portion 36 with rounded edges may be equally well tolerated. Other appropriate designs may be determined by those skilled in the art. For example, the plan view of the head portion may be round or ovular (see, e.g., FIGS. 1, 3, 5A-5C, 6-8, and 10) or square or rectangular (see, e.g., FIG. 9). The inner (convex) surface of the head portion 36 may be flat or curved (or a combination of both), as appropriate, to correspond to the shape of the external surface of the sclera, if the drainage device 30 is to be positioned subconjunctivally. In general, a subconjunctival placement of at least the head portion 36 may result in a lower risk of extrusion.

In some aspects, the drainage device 30 may comprise a filter 40 (see, e.g., FIG. 4) and/or a flow control device 39 (see, e.g., FIG. 13) for maintaining and/or controlling intraocular pressure and for allowing for a more physiological dynamic of the aqueous humor. In such aspects, the head portion 36 of the outlet assembly 34 may be configured to house the flow control device 39 and/or the filter 40, or may otherwise define an opening for receiving the flow control device 39, through which opening the filter 40 may also be inserted into and/or removed from the head portion 36.

FIG. 4 schematically illustrates, for example, a filter 40 at least partially disposed within the head portion 36 and/or the lumen 46 at the proximal end 42 of the tubular body 32 of the drainage device 30. In one aspect, the filter 40 may be configured as an elongate member having a distal inflow end 44 and a proximal outflow end 42. As shown in FIG. 4, for example, the filter 40 may be configured to extend laterally across the lumen 46 such that the lumenal passage of the tubular body 32 is closed or substantially closed by the filter 40. The aqueous humor flowing through the lumen 46 is therefore directed through the filter 40, wherein the filter 40 filters the aqueous humor to prevent bacterial migration in either direction along the lumen. The filter 40 may also be configured to regulate or at least facilitate the regulation of intraocular pressure by providing a predetermined resistance to outflow of aqueous humor from the anterior chamber of the eye to the external location (i.e., into the tear film about the exterior surface of the eye). In some aspects the filter 40 may be configured as a resistive component for the flow of aqueous humor. That is, the filter can provide particular flow rate of aqueous humor by selecting filter characteristics such as a predetermined number and size of pores and a selected overall length of the filter 40 (i.e., the flow path). These parameters, either separately or in combination, may be configured to provide an appropriate resistance to the flow of aqueous humor sufficient to reduce and maintain intraocular pressure, while preventing ocular hypotony. The filter 40 may have a gradient of pore sizes along the length of the filter 40. For example, the pore size may continually decrease from the distal end 44 of the filter 40 to the proximal end 42 in order to prevent debris accumulation at the distal (inlet) end 44 of the filter 40. Larger pores sizes at the distal end 44 and at the proximal end 42 of the filter 40 may provide a pore gradient, which may help to reduce the effect of clogging on the outflow resistance. A representative filter 40 or a layer or portion thereof may have a pore size of, for example, 0.5 µm or less to minimize or prevent bacterial migration therethrough. In instances where the filter 40 comprises multiple layers or portions, other layers or portions may have a pore size greater than 0.5 µm in order to reduce debris or relatively large contaminants.

In some aspects, the filter 40 may be removable and replaceable, and may be facilitated by external access to the outlet assembly 34, or by external access to the tubular body 32 by way of the outlet assembly 34, without disrupting the position of the drainage device 30 (i.e., the tubular body 32 thereof) in the eye. By replacing the filter 40, for example, the ocular pressure can be regulated by selecting a filter configuration that provides a selected aqueous humor flow rate. Alternatively, the filter 40 may be configured to form a permanent element of the drainage device 30.

In some aspects, a flow control device 39 (see, e.g., FIG. 13A) may be housed by, in fluid communication with, or otherwise operably engaged with the head portion 36 (i.e., a housing defined and provided by the head portion 36). If the filter 40 is implemented in such aspects, the filter 40 may be disposed in fluid communication between the inlet (distal) end 44 of the tubular body 32 and the flow control device 39, with the filter 40 being configured to filter contaminants from the aqueous humor prior to the flow control device 39. In other instances, the filter 40 may be engaged with the housing of the head portion 36 subsequent to the outlet (proximal) end 42 of the tubular body (or "tube") 30, and wherein the housing of the head portion 36 is configured such that the flow control device 39 operably engaged therewith is removable or replaceable with respect to the housing, so as to also allow the filter 40 to be removed or replaced. In still other aspects, the filter 40 may be disposed in fluid communication with the flow control device 39, opposite to the outlet (proximal) end 42 of the tubular body 32 from the flow control device 39, wherein the filter 40 is configured to filter contaminants from any backflow to the flow control device 39. In such instances, the filter 40 may be engaged with the housing of the head portion 36 subsequent to the flow control device 39, and wherein the housing may be configured such that the filter 40 engaged therewith subsequent to the flow control device 39 is removable or replaceable with respect to the housing. In still other instances, for example, in a "dual filter" configuration, a filter 40 may be disposed both upstream and downstream of the flow control device 39 (see, e.g., a dual filter configuration housed by the head portion 36, as shown in FIG. 13A). Representative configurations of filters and flow control devices associated with drainage devices of the type disclosed herein are disclosed, for example, in U.S. patent application Ser. No. 14/473,228, filed Aug. 29, 2014; and Ser. No. 14/826,866; filed Aug. 14, 2015, each to Camras et al., and each of which is incorporated herein by reference.

For example, as disclosed in U.S. patent application Ser. No. 14/826,866 to Camras et al.; filed Aug. 14, 2015, and previously incorporated herein by reference, the flow control device 39 may define a conduit in communication between the cavity and the drainage site (i.e., wherein the flow control device 39 is engaged with the housing/head portion 36 or, according to some aspects of the disclosure, the tubular member 100), wherein the conduit may be dilatable in response to the intraocular pressure being above a preselected pressure by controlling the flow of the aqueous humor from the cavity 52 and through the distal end of the channel 150 to the drainage site. Such dilation of the conduit may increase the flow, or decrease resistance to the flow, of the aqueous humor through the conduit to the drainage site, thereby reducing the intraocular pressure to no greater than the preselected pressure. In some instances, the flow control device 39 may comprise a relatively thin and flexible membrane defining a conduit 38 in the form of an elongate slit (not shown), wherein the flexible membrane is configured to deform about a medial portion along the length of the slit, in response to elevated intraocular pressure, to allow aqueous humor to exit the drainage device 30. In other aspects, such as shown, for example, in FIGS. 13A, and 13B, the flow control device 39 may comprise an elongate or relatively thick portion defining a conduit 38 extending through the thickness. In particular instances, the conduit 38 is dilatable in response to the intraocular pressure being above a preselected or threshold pressure, to increase the flow or to decrease resistance to flow of the aqueous humor through the conduit 38 to the external location or drainage site (i.e., the external ocular surface) and to reduce and/or stabilize the intraocular pressure to no greater than the preselected pressure. For example, the configuration of the dilatable conduit 38 may be determined according to a preselected intraocular pressure, wherein the preselected ocular pressure may be a factor of, for example, the patient's age, physical characteristics, characteristics of the eye, advancement of the condition, particular physiological dynamics, or the like that are particular to a particular patient. The lateral cross-section of the conduit 38 may take different forms such as, for example, circular, ovular, square, rectangular, or any other suitable shape, whether regular or irregular.

The flow control device 39, or at least the portion thereof defining the conduit 38, may be comprised of a flexible biocompatible material such as, for example, polyurethane or silicone. In some instances, the flow control device 39, or the material from which the flow control device 39 is comprised, may be configured to be responsive, for example, to an output of a laser device (not shown) so as to form or open additional dilatable channels therein or to attach components together. That is, a laser light output directed at the material comprising the flow control device 39 may cause the formation or opening of additional conduits 38, as necessary or desired for controlling the flow of aqueous humor from the eye, and thus controlling the intraocular pressure. In particular instances, the flow control device 39, or the material from which the flow control device 39 is comprised, may also be configured to be responsive, for instance, to the output of the laser device to seal or constrict a conduit 38 defined thereby. That is, one or more of the conduits 38 can be sealed or constricted, as necessary or desired, to control the flow or manipulate the resistance to flow of aqueous humor from the eye. In particular aspects, the laser modification of the conduits defined by the flow control device 39, or the material from which the flow control device 39 is comprised, may be accomplished in situ, with the drainage device 30 in place with respect to the eye. The flow control device 39 may be fabricated by any suitable microfabrication technique or process, in addition or in the alternative to the responsiveness thereof to the output of a laser device. For example, photolithography/deposition techniques, casting, molding, or any other suitable technique or combinations thereof may be implemented for forming the flow control device 39.

As disclosed herein, the head portion/housing 36 may be configured to define a cavity 52 therein. For example, the head portion/housing 36 may be comprised of two or more portions which, when assembled, cooperate to define the cavity 52 therein (see, e.g., FIG. 5B). The cavity 52, in communication with the lumen 46 of the tubular body (or a first tube) 32, is thus configured to receive the aqueous humor from the anterior chamber through the proximal outflow end 42 of the tubular body 32. The aqueous humor received by the cavity 52 may then be drained from the cavity 52 to a drainage site disposed distally to the cavity 52. As such, in some instances (see, e.g., FIGS. 1 and 3-10), the drainage device 30 may further include an elongate tubular member (or a second tube) 100 having opposed proximal and distal ends 110, 120, with the tubular member 100 further defining a longitudinally-extending channel 150. The proximal end 110 of the tubular member 100 is engaged with or disposed in the housing/head portion 36, independently of the tubular body 32, such that the channel 150 defined by the tubular member 100 is in fluid communication with the cavity 52, and such that the distal end 120 is spaced apart from the housing/head portion 36. That is, the tubular member 100 is configured to be engaged with the housing/head portion 36, and the housing/head portion 36 is configured to be separately, discretely, and independently engaged with the tubular body 32. The channel 150 defined by the tubular member 100 is configured to receive the aqueous humor from the cavity 52 through a proximal opening at the proximal end 110 and to direct the aqueous humor through a distal opening at the distal end 120 to a drainage site disposed distally to, externally to, or otherwise away from the anterior chamber and the housing/head portion 36. As shown in FIG. 3, for example, the tubular body 32 may extend along a first axis and the tubular member 100 may extend along a second axis, where the second axis is perpendicular to the first axis.

The tubular member 100, in some aspects, may provide a single outlet for the aqueous humor from the cavity 52 of the housing/head portion 36 as shown, for example, in FIGS. 3, 4, and 8-10. That is, the single tubular member 100 having the proximal end 110 thereof engaged with the housing/head portion 36 and extending therefrom, may define a single channel 150 in communication the cavity 52 for directing the aqueous humor to the distal drainage site away from the housing/head portion 36. In other instances, however, the tubular member 100 may be configured such that the channel 150 is bifurcated along a portion of the tubular member 100, distal to the housing/head portion 36, to form two (or more) outlet channels 160, 170 (see, e.g., FIGS. 10, 11A-B, and 12A-B). In such instances, for example, the channel 150 may extend from the cavity 52 and to each of the outlet channels 160, 170, wherein the outlet channels 160, 170 then extend to the distal end 120 of the tubular member 100. In another example, the outlet channels 160, 170 may each extend directly from the cavity 52, wherein the single channel 150 is not present in the tubular member 100. Since the tubular member 100 may lie on the conjunctival surface when the drainage device 30 is implanted, the tubular member 100 may have an appropriate coating applied thereto so as to facilitate comfort of the patient (i.e., by lowering the sensation of the tubular member 100 being a foreign object in the eye).

In still other instances, a diverter 200 may be engaged with the distal end 120 of the tubular member 100, with the diverter 200 having at least two elongate diversion members 210, 220 extending from the distal end 120 of the tubular member 100. In such instances, each diversion member 210, 220 may define a diversion channel 230, 240 in communication with the channel 150 defined by the tubular member 100 (see, e.g., FIGS. 1, 5A-5C, and 6). The diverter 200 or the diversion members 201, 220 thereof may be configured, for example, to cooperate with the tubular member 100 to form a Y-arrangement or a T-arrangement (see, e.g., the various "T" arrangements shown in FIGS. 1, 5A-5C, and 6). With such various configurations, for instance, the drainage device 30 may be configured such that the tubular body 32 and the housing/head portion 36 are implanted under the conjunctival surface (i.e., to prevent or minimize the risk of extrusion), while the tubular member 100 and/or the diverter 200 are configured, for example, to cooperate to extend out of the plane of the housing/head portion 36, such that the tubular member 100 and/or diverter 200/diversion members 201, 220 lie on top of the conjunctival surface when the drainage device 30 is implanted (see, e.g., the configurations shown in FIGS. 5A-5C, and 6) to direct the aqueous humor to the drainage site(s). One skilled in the art will appreciate, however, that the drainage device 30 may also be configured such that the housing/head portion 36 can lie on the conjunctival surface to facilitate replaceability of the filter 40 and/or flow control device 39 therein, if necessary, without removing the entire implanted drainage device 30. In some aspects, each diversion member 210, 220 includes a proximal end 210A, 220A engaged with the distal end 120 of the tubular member 100, and an opposing distal end 210B, 220B (see, e.g., FIG. 1). In such aspects, it may be preferred that the tubular member 100 is configured to only allow flow of the aqueous humor outwardly of the distal end 120 thereof from the cavity 52. Since the diverter 200 may lie on the conjunctival surface when the drainage device 30 is implanted, the diverter 200 may have an appropriate coating applied thereto so as to facilitate comfort of the patient (i.e., by lowering the sensation of the tubular member 100/diverter 200 being a foreign object in the eye).

In some aspects, the tubular member 100 and/or the diverter 200 may be configured to control a flow of the aqueous humor from the cavity 52 to the drainage site (i.e., the external ocular surface of the eye). That is, in some instances, the tubular member 100 and/or the diversion member(s) 210, 220 may include a flow resistance element or arrangement (i.e., filter 40 and/or flow control device 39) configured to control or regulate the flow of the aqueous humor from the cavity 52. According to some aspects, the flow resistance arrangement may comprise a slit or slit valve arrangement disposed about the distal end(s) of the tubular member 100 or the diverter 200. In other aspects, the flow resistance element or arrangement may include one or more of a flow control device 39, a filter or filter device 40, or a flow control device 39 and a filter or filter device 40, engaged with the tubular member 100 or the diverter 200, or between the housing/head portion 36 and the proximal end 110 of the tubular member 100. In some instances, the flow control device 39 and/or filter 40 may be configured to be removable or replaceable with respect to the housing/head portion 36, the tubular member 100 and/or the diversion member(s) 210, 220. In some such instances, the tubular member 100 and/or the diversion member(s) 210, 220 may be configured to be collapsible on removal of the flow resistance element or arrangement, so as to, for example, prevent hypotony or backflow of contaminants through the diversion member(s) 210, 220 or tubular member 100, into and toward the cavity 52 and the anterior chamber of the eye. An appropriate tool configured to engage the flow resistance element or arrangement for removal or replacement with respect to the tubular member 100 and/or the diversion member(s) 210, 220. In this manner, the risk of infection may be lowered. In addition, if necessary or desired, a medicinal agent applied to the flow resistance element or arrangement for preventing occlusion or bacterial contamination thereof by inhibiting the formation of fibrotic membranes, inflammatory membranes, bacterial adhesions, or biofilms. Further, and in accordance with such arrangements, one or more filters 40 may be disposed in fluid communication between the flow control device 39 and the distal end 120 of the tubular member 100, wherein the filter(s) 40 is/are configured to filter contaminants from any backflow to the flow control device 39 from the drainage site. In such instances, the filter 40 may be engaged with the tubular member 100 subsequent to the housing/head portion 36.

In some aspects, the tubular member 100 having the filter 40 and/or the flow control device 39 engaged therewith, whether within the channel 150 or between the proximal end 110 and the housing/head portion 36, may be configured to be removable or replaceable with respect to the housing/head portion 36. In other aspects, the diverter 200 or diversion members 210, 220 having the filter 40 and/or the flow control device 39 engaged therewith, for example, within one of the diversion channels 230, 240, may be configured to be removable or replaceable with respect to the tubular member 100. In either instance, the filter 40 and/or flow control device 39 may be removable or replaceable with respect to the tubular member 100 and/or the diverter 200, upon removal of the tubular member 100 from engagement with the housing/head portion 36, or upon removal of the diverter 200 from engagement with the tubular member 100, as appropriate. Such a removal/replacement procedure may involve, for example, a clamp applied to the housing or interface with the tubular member to cease any flow of the aqueous humor from the anterior chamber or cavity, while forceps can be used to remove and replace the tubular element. In some instances, the filter(s) 40 and/or flow control device 39 may include one or more provisions for facilitating removability and replaceability, for example, with the aide of an appropriate tool. For instance, the filter(s) 40 and/or flow control device 39 may include a slot or protrusion to facilitate interaction with an appropriate removal/replacement tool, whether forceps or otherwise.

The flow resistance element or arrangement (i.e., one or more filters 40 and/or a flow control device 40) and/or the tubular member 100 or diverter 200 receiving and housing the same, may be configured in different manners to facilitate removal/replacement. For example, in addition to, or instead of, the tubular member 100 and/or the diversion member(s) 210, 220 being configured to be collapsible on removal of the flow resistance element or arrangement (i.e., to prevent hypotony), the flow resistance element or arrangement may be configured to expand in size upon insertion into the tubular member 100 and/or the diversion member(s) 210, 220 for securement therein. In another instance, the resistance to flow provided by the flow resistance element or arrangement, may be adjusted or modified in different manners. For example, a length or inner diameter of the tubular member 100 and/or the diversion members 210, 220 may be adjusted, or different multiples or configurations of flow resistance elements (i.e., filters 40 and/or flow control devices 39), each having an effect on the resistance to flow, may be implemented. For example, a filter with smaller pore size, lower pore density, thicker or/and smaller surface area will result in increased flow resistance, thereby decreasing the flow of aqueous humor therethrough, while a filter with larger pore size, higher pore density, thinner and/or larger surface area will result in decreased flow resistance, thereby increasing the flow of aqueous humor therethrough. In other instances, sutures may be used to constrict the tubular member 100 and/or the diversion member(s) 210, 220 to increase resistance to flow of the aqueous humor, while, for example, a laser pulse or cutting device may be used to loosen or cut the suture(s) to otherwise decrease resistance to flow of the aqueous humor.

In instances of the tubular member 100 implementing bifurcated channels 160, 170, or of the drainage device 30 including a diverter 200 engaged with the tubular member 100, the bifurcated channels 160, 170 of the tubular member 100 and/or the diversion channels 230, 240 of the diverter 200 may be configured to facilitate flushing/cleaning in situ. For example, in some instances, one of the bifurcated channels 160, 170 of the tubular member 100 may be configured to allow an inflow from the distal end 120 toward and up to the cavity 52 such that the tubular member 100 can be flushed to remove debris. That is, the housing/head portion 36 or the interface between the housing and the tubular member 100 can be engaged by a clamp to prevent flow into or out of the housing via the tubular member 100. A cleaning solution can then be directed into the one of the bifurcated channels 160, 170 configured to allow an inflow, such that the cleaning solution is directed inwardly along that bifurcated channel 160, 170, and out through the other bifurcated channel 160, 170, such that any contaminants are flushed out of the tubular member 100. Similarly, in instances where a diverter 200 is implemented, one of the diversion members 210, 220 may be configured to allow an inflow from the distal end 210B, 220B thereof, wherein the inflow into the one of the diversion members 210, 220 may be used to flush out the diversion members 210, 220, without the inflow entering the distal end of the channel 150 defined by the tubular member 100. That is, the distal end 120 of the tubular member 100 can be engaged by a clamp to prevent flow into or out of the tubular member 100. A cleaning solution can then be directed into the one of the diversion channels 230, 240 configured to allow an inflow, such that the cleaning solution is directed inwardly along that diversion channel 230, 240, and out through the other diversion channel 230, 240, such that any contaminants are flushed out of the diverter 200.

In addition to the materials already described herein, the tube/tubular body 32 and the outlet assembly (housing/head portion 36, tubular member 100, and diverter 200) of the embodiments of drainage device 30 may be formed from materials having good biocompatibility and durability, and which are sufficiently flexible. Suitable materials include a material selected from the group consisting of silicone, acrylic, polyimide, polypropylene, polymethyl methacrylate, polytetrafluoroethylene, hydrogels, polyolefin, polyolefin resins such as polyethylene, polyisobutylene, ethylene-vinyl acetate copolymer, polynorbornene, polyvinylchloride, polyester, polyvinyl alcohol, polyvinyl pyrolidone, polyethersulfone (PES), poly(styrene-isobutyl-styrene), polysilicon, polyurethane, polycarbonate urethane, glass and ceramics such as alumina and titania, metals such as stainless steel, titanium, gold, silver, platinum or nitinol, collagen or chemically-treated collagen, hydroxyapetite, natural and synthetic rubbers such as polybutadiene, polyisoprene, SBR (Styrene Butadiene Rubber), and SIR, polyacetal resin, ABS (Acrylonitrile-Butadiene-Styrene) resin, solid HEMA polymer, and combinations thereof.

At least a portion of the filter(s) 40 has a pore size that is sufficiently small to prevent ingress or backflow of microorganisms, such as bacteria, viruses, fungi and spores thereof, from entering the lumen 46, so as to minimize the opportunity for reflux infection in the eye. A pore size of less than about 0.4 µm or 0.5 µm is sufficiently small to prevent ingress or backflow of microorganisms past the filter(s) 40. In some embodiments, the filter 40 may comprise a microporous/nanoporous membrane or polymer network, fiber network, or microcapsular material having a network of pores. Microporous filter membranes suitable for use with ophthalmic devices include micropore filter membranes (polycarbonate, polyethersulfone, polyvinylidene fluoride, polytetrafluoroethylene), porous hydrogels (polyacrylamide, alginate, polyhydroxyethylmethacrylate), and microperforated silicone or polyvinyl polymer, such as polyvinyl alcohol, which is expandable within the lumen 46. Other suitable polymers include a polyolefin polymer, an ethylene-vinyl alcohol copolymer, a polyacrylonitrile polymer, a polyurethane polymer, a cellulose polymer, cellulose acetate polymer, a polyimide polymer, and a polyamide polymer. Filter membrane nanotechnology may also be useful to fabricate microporous membranes to be biocompatible, non-degradable, and immune-isolating. Other materials, such as ceramics, polymers and metals, such as titanium, may also be suitable for the filter. The filters may be created using additive manufacturing, lithography or electrospinning. In some instances, the filter 40 may have an antibiotic coating to prevent contamination during replacement. Suitable coatings for the filter are described in co-pending U.S. Patent Application Publication No. 2010/0057055, the contents of which are hereby incorporated by reference in their entirety.

At least a portion of the external surfaces of the tube/tubular body 32, the suture bars 50, the inner surface of the head portion 36, the tubular member 100, and/or the diverter 200 of the drainage device 30 may be coated with a porous cellular ingrowth material. The porous cellular ingrowth material is coated on at least the portion of the drainage device 30 that is in contact with the sclera and conjunctiva when the drainage device 30 is implanted so as to promote ingrowth with respect to that selected portion of the drainage device 30. That is, in aspects where it may be necessary or desirable for the tubular member 100 or diverter 200 to be removable or replaceable with respect to the subconjunctivally-implanted housing/head portion 36, the portion of the tubular member 100 extending through or otherwise in contact with the conjunctiva may include the porous cellular ingrowth material so as to promote ingrowth, integration, and conjunctival closure with respect thereto. In other aspects, a collar 180 (see, e.g., FIG. 10) may extend, as a separate and discrete component, over an interface between the tubular member 100 and the housing/head portion 36

(i.e., as a sleeve over the interface), or the collar 180 may form a portion of the tubular member 100, wherein the tubular member 100 may be cut or otherwise removed from the collar 180 for removal or replacement. In such instances, the tubular member 100 or diverter 200 can be removed and replaced without disturbing the conjunctiva (i.e., such that the tubular member 100/diverter 200 is not removed or replaced within the conjunctival space). Such a provision may thus reduce the risk of infection and/or prevent epithelial downgrowth. The porous cellular ingrowth material may be applied in the form of a coating, such as a hydroxyapatite or porous polyethylene, which serves to promote cell adhesion. In other aspects, a component, such as the collar 180, may be comprised of a porous cellular ingrowth material, such as porous polyethylene. Selected growth factors may be adsorbed such that the tube/tubular body 32, the suture bars 50, and the housing/head portion 36 of the drainage device 30 may be securely anchored in position. This enables the drainage device 30 to resist in situ motion and displacement. To further promote tissue ingrowth and cell attachment, the body of the drainage device 30 may include surface alterations, such as texturing, roughening or other patterned or non-patterned irregularities.

The remaining surfaces of the drainage device 30, including the entire lumenal surface, the portions of the external surface of the drainage device not in contact with the sclera, and/or the filter surfaces, may be coated with a bio-inert surface coating to enhance surface biocompatibility. Such coatings may include bio-inert polymer coatings such as phosphoryl choline (PC), polyethylene glycol (PEG), sulfobetaine (SB), carboxybetaine (CB), and polyethylene oxide (PEO). These polymer coatings down-regulate deleterious biological reactions, primarily by attracting a large and stable hydration shell when grafted onto a surface. Bio-inert surface coatings may be further modified with biologically active molecules such as heparin, spermine, surfactants, proteases or other enzymes, or other biocompatible chemicals amendable to surface immobilization. PEO also is amenable to end-group coupling for surface immobilization of the biologically active molecules. The addition of such bioactive molecules could advantageously impart specific desired functionality, for example, allowing a further increase in the hydrophilicity of the surface.

The coating for the drainage device 30 can also comprise material that includes a therapeutic agent, as well as antifibrotic and/or antimicrobial and/or anti-fouling agents. The therapeutic agent can be selected from the group consisting of heparin, selenium, TGF-beta, an intraocular pressure-lowering drug, and an anti-proliferative agent. The coatings can be, for example, a drug eluting coating, an antithrombogenic coating, and/or a lubricious coating. Materials that may be used for a drug-eluting coating include parylene C, poly(butyl methacrylate), poly(methyl methacrylate), polyethylene-co-vinyl acetate, and other materials known in the art. Anti-microbial coatings may include, for example selenium, silver, melimine, or fimbrolides or other quorum sensing inhibitors. In addition, these agents may be incorporated into the filter material or other components of the drainage device 30 via covalent, metallic, ionic, or non-covalent bonding, or by surface adsorption.

Another aspect of the disclosure herein is directed to a method of manufacturing an apparatus for draining aqueous humor from an eye for reducing and/or stabilizing intraocular pressure, as shown, for example, in FIG. 14. Such a method comprises engaging an outlet end of a tube into fluid communication with a cavity defined by a housing, wherein the outlet end extends to an inlet end adapted to be in fluid communication with the anterior chamber of the eye, and wherein the tube is adapted to direct a flow of aqueous humor from the anterior chamber and through the inlet end and to the outlet end such that the aqueous humor is received by the cavity (block 300). As shown in block 320, a proximal end of an elongate tubular member is engaged with the housing, independently of the tube/tubular body 32, wherein the tubular member has a distal end opposing the proximal end and defines a longitudinally-extending channel, such that the channel defined by the tubular member is in fluid communication with the cavity and such that the distal end is spaced apart from the housing, and wherein the channel is configured to receive the aqueous humor from the cavity and to direct the aqueous humor through the distal end to a drainage site disposed distally to the anterior chamber and to the housing. Such a method of manufacture may be realized in conjunction with the drainage device(s) and components thereof as disclosed herein.

In relation to such a method of manufacture, a flow control device may be operably engaged with the housing or the tubular member, wherein the flow control device is configured to control the flow of the aqueous humor from the cavity and through the distal end of the channel to the drainage site. In some aspects, a flow control device, defining a conduit in communication between the cavity and the drainage site, may be engaged with the housing, wherein the conduit is dilatable in response to the intraocular pressure being above a preselected pressure, so as to increase the flow or to decrease resistance to the flow of the aqueous humor through the conduit to the drainage site and to reduce the intraocular pressure to no greater than the preselected pressure.

In other aspects, a filter device may be disposed in fluid communication between the inlet end of the tube and the flow control device, wherein the filter device is configured to filter contaminants from the aqueous humor prior to the flow control device. In some instances, the filter device may be with the housing subsequent to the outlet end of the tube, with the housing being configured such that the flow control device operably engaged therewith is removable or replaceable with respect to the housing, so as to allow the filter device to be removed or replaced. The filter device may be disposed in fluid communication between the flow control device and the distal end of the tubular member, with the filter device being configured to filter contaminants from any backflow to the flow control device from the drainage site. In yet other instances, the filter device may be engaged with the housing subsequent to the flow control device, with the housing being configured such that the filter device engaged therewith is removable or replaceable with respect to the housing. In other instances, the filter device may be engaged with the tubular member subsequent to the housing, particularly wherein the tubular member is engaged with the filter device such that the tubular member and the filter device are configured to be removable or replaceable with respect to the housing, and such that the filter device is configured to be removable or replaceable with respect to the tubular member.

In still other aspects, an anchoring device may be operably engaged with the tube or the housing, with the anchoring device being configured to engage the eye subconjunctivally so as to secure at least the tube or the housing to the eye.

A flow resistance element may be engaged with the tubular member, with the flow resistance element including a flow control device, a filter device, or a flow control device and a filter device, wherein the flow resistance element is configured to be removable or replaceable with respect to the tubular member, and wherein the tubular member is configured to be collapsible on removal of the flow resistance element.

In yet other aspects, a medicinal agent may be applied to the flow resistance element for preventing occlusion or bacterial contamination thereof by inhibiting the formation of fibrotic membranes, inflammatory membranes, bacterial adhesions, or biofilms. In still other embodiments, an external portion of the elongate tubular member may be coated for increasing patient comfort.

In a further aspect, the proximal end of the elongate tubular member may be engaged with the housing, wherein the channel defined by the tubular member is bifurcated along a portion of the tubular member distal to the housing. In some instances, one of the bifurcated channels may be configured to allow an inflow from the distal end to the cavity.

In some embodiments, a diverter may be engaged with the distal end of the tubular member, with the diverter having at least two elongate diversion members extending from the distal end of the tubular member, and with each diversion member defining a diversion channel in communication with the channel defined by the tubular member. The diverter may be configured to cooperate with the tubular member to form a Y-arrangement or a T-arrangement. In some instances, each diversion member includes a proximal end engaged with the distal end of the tubular member, and an opposing distal end, wherein the tubular member is configured to only allow flow of the aqueous humor outwardly of the distal end thereof from the cavity. In other instances, one of the diversion members may be configured to allow an inflow from the distal end thereof, wherein the inflow into the one of the diversion members is used to flush out the diversion members, without the inflow entering the distal end of the channel defined by the tubular member.

Many modifications and other aspects of the disclosure will come to mind to one skilled in the art to which this disclosure pertains having the benefit of the teachings presented in the foregoing descriptions and the associated drawings. For example, the tubular member 100 and/or the diverter 200, particularly in instances where one of the bifurcated channels 160, 170, or one of the diversion channels 230, 240, is configured to permit and inflow, may be used to infuse drugs, medications, or other substances back through the drainage device 30 and into the anterior chamber of the eye. In another example, the tubular member 100 and/or the diverter 200 may be at least partially porous so as to allow the aqueous humor to be discharged from the cavity 52 of the housing more uniformly onto the ocular surface, which may help to alleviate a dry eye condition. Therefore, it is to be understood that the disclosure is not to be limited to the specific aspects disclosed herein and that modifications and other aspects are intended to be included within the scope of the appended claims. Although specific terms are employed herein, they are used in a generic and descriptive sense only and not for purposes of limitation.

What is claimed is:

1. An apparatus for draining aqueous humor from an eye for reducing intraocular pressure, the eye having an anterior chamber and including a cornea, a surrounding marginal limbus by which the cornea is continuous with a scleral layer and a conjunctival layer, and an external ocular surface of the eye under an eyelid, the apparatus comprising:
   a first tube extending, along a first axis, between an inlet end and an outlet end, the inlet end being adapted to be in fluid communication with the anterior chamber of the eye, and the first tube being adapted to direct a flow of aqueous humor from the anterior chamber and through the inlet end to the outlet end;
   a housing defining a cavity in fluid communication with the outlet end of the first tube, the cavity being configured to receive the aqueous humor;
   a second tube extending along a second axis, the second axis being perpendicular to the first axis of the first tube, the second tube having opposed proximal and distal ends and defining a longitudinally-extending channel, the second tube having a proximal opening disposed at the proximal end and a distal opening disposed at the distal end, the proximal end of the second tube being disposed in the housing and the distal end being spaced from the housing, the channel being in fluid communication with the cavity and configured to receive, through the proximal opening, the aqueous humor from the cavity and to direct the aqueous humor through the distal opening to a drainage site disposed distally to the anterior chamber and to the housing; and
   a flow control device operably engaged with the second tube and configured to control the flow of the aqueous humor from the cavity and through the distal opening of the second tube to the drainage site.

2. The apparatus of claim 1, wherein the flow control device defines a conduit in communication between the cavity and the drainage site, the conduit being dilatable in response to the intraocular pressure being above a preselected pressure, to increase the flow or to decrease resistance to the flow of the aqueous humor through the second tube to the drainage site and to reduce the intraocular pressure to no greater than the preselected pressure.

3. The apparatus of claim 1, comprising a filter device disposed in fluid communication between the inlet end of the first tube and the flow control device, the filter device being configured to filter contaminants from the aqueous humor prior to the flow control device.

4. The apparatus of claim 3, wherein the filter device is engaged with the housing subsequent to the outlet end of the first tube, and wherein the housing is configured such that the flow control device operably engaged therewith is removable or replaceable with respect to the housing, so as to allow the filter device to be removed or replaced.

5. The apparatus of claim 1, comprising a filter device disposed in fluid communication between the flow control device and the distal end of the second tube, the filter device being configured to filter contaminants from any backflow to the flow control device from the drainage site.

6. The apparatus of claim 5, wherein the filter device is configured to be removable or replaceable with respect to the second tube.

7. The apparatus of claim 5, wherein the filter device is engaged with the second tube.

8. The apparatus of claim 7, wherein the second tube having the filter device engaged therewith is configured to be removable or replaceable with respect to the housing, and the filter device is configured to be removable or replaceable with respect to the second tube.

9. The apparatus of claim 1, comprising an anchoring device operably engaged with the first tube or the housing, the anchoring device being configured to engage the eye subconjunctivally so as to secure at least the first tube or the housing to the eye.

10. The apparatus of claim 1, wherein the second tube is configured to be collapsible on removal of the flow control device.

11. The apparatus of claim 1, further comprising a medicinal agent applied to the flow control device for preventing occlusion or bacterial contamination thereof by inhibiting the formation of fibrotic membranes, inflammatory membranes, bacterial adhesions, or biofilms.

12. The apparatus of claim 1, wherein the channel is bifurcated along a portion of the second tube distal to the housing.

13. The apparatus of claim 12, wherein one of the bifurcated channels is configured to allow an inflow from the distal end to the cavity.

14. The apparatus of claim 1, comprising a diverter engaged with the distal end of the second tube, the diverter having at least two elongate diversion members extending from the distal end of the second tube, with each diversion member defining a diversion channel in communication with the channel defined by the second tube.

15. The apparatus of claim 14, wherein the diverter is configured to cooperate with the second tube to form a Y-arrangement or a T-arrangement.

16. The apparatus of claim 14, wherein each diversion member includes a proximal end engaged with the distal end of the second tube, and an opposing distal end, and wherein the second tube is configured to only allow flow of the aqueous humor outwardly of the distal end thereof from the cavity.

17. The apparatus of claim 16, wherein one of the diversion members is configured to allow an inflow from the distal end thereof, wherein the inflow into the one of the diversion members is used to flush out the diversion members, without the inflow entering the distal end of the channel defined by the second tube.

18. The apparatus of claim 1, wherein an external portion of the second tube is coated for increasing patient comfort.

19. The apparatus of claim 1, wherein at least a portion of the second tube is configured to extend through the conjunctival layer upon implantation of the apparatus, and the at least a portion of the second tube is coated with or is comprised of a porous cellular ingrowth material.

20. A method of manufacturing an apparatus for draining aqueous humor from an eye for reducing intraocular pressure, the eye having an anterior chamber and including a cornea, a surrounding marginal limbus by which the cornea is continuous with a scleral layer and a conjunctival layer, and an external ocular surface of the eye under an eyelid, the method comprising:
engaging an outlet end of a first tube into fluid communication with a cavity defined by a housing, the first tube extending, along a first axis, between an inlet end and the outlet end, the inlet end adapted to be in fluid communication with the anterior chamber of the eye, the first tube being adapted to direct a flow of aqueous humor from the anterior chamber and through the inlet end and to the outlet end such that the aqueous humor is received by the cavity;
engaging a proximal end of a second tube with the housing, the second tube extending along a second axis, the second axis being perpendicular to the first axis of the first tube, the second tube having a distal end opposing the proximal end and defining a longitudinally-extending channel, the second tube having a proximal opening disposed at the proximal end and a distal opening disposed at the distal end, the proximal end of the second tube being disposed in the housing and the distal end being spaced from the housing, the channel being in fluid communication with the cavity and configured to receive, through the proximal opening, the aqueous humor from the cavity and to direct the aqueous humor through the distal opening to a drainage site disposed distally to the anterior chamber and to the housing; and
operably engaging a flow control device with the second tube, the flow control device being configured to control the flow of the aqueous humor from the cavity and through the distal opening to the drainage site.

21. The method of claim 20, wherein the flow control device defines a conduit in communication between the cavity and the drainage site, the conduit being dilatable in response to the intraocular pressure being above a preselected pressure, to increase the flow or to decrease resistance to the flow of the aqueous humor through the conduit to the drainage site and to reduce the intraocular pressure to no greater than the preselected pressure.

22. The method of claim 20, comprising disposing a filter device in fluid communication between the inlet end of the tube and the flow control device, the filter device being configured to filter contaminants from the aqueous humor prior to the flow control device.

23. The method of claim 22, wherein disposing a filter device in fluid communication between the inlet end of the first tube and the flow control device comprises engaging the filter device with the housing subsequent to the outlet end of the first tube, with the housing being configured such that the flow control device operably engaged therewith is removable or replaceable with respect to the housing, so as to allow the filter device to be removed or replaced.

24. The method of claim 20, comprising disposing a filter device in fluid communication between the flow control device and the distal end of the second tube, the filter device being configured to filter contaminants from any backflow to the flow control device from the drainage site.

25. The method of claim 24, wherein the filter device is configured to be removable or replaceable with respect to the second tube.

26. The method of claim 24, wherein the filter device is engaged with the second tube.

27. The method of claim 26, wherein the second tube and the filter device are configured to be removable or replaceable with respect to the housing, and such that the filter device is configured to be removable or replaceable with respect to the second tube.

28. The method of claim 20, comprising operably engaging an anchoring device with the first tube or the housing, the anchoring device being configured to engage the eye subconjunctivally so as to secure at least the first tube or the housing to the eye.

29. The method of claim 20, comprising wherein the second tube is configured to be collapsible on removal of the flow control device.

30. The method of claim 20, comprising applying a medicinal agent to the flow control device for preventing occlusion or bacterial contamination thereof by inhibiting the formation of fibrotic membranes, inflammatory membranes, bacterial adhesions, or biofilms.

31. The method of claim 20, wherein the channel defined by the second tube is bifurcated along a portion of the second tube distal to the housing.

32. The method of claim 31, wherein one of the bifurcated channels is configured to allow an inflow from the distal end to the cavity.

33. The method of claim 20, comprising engaging a diverter with the distal end of the second tube, the diverter having at least two elongate diversion members extending from the distal end of the second tube, with each diversion member defining a diversion channel in communication with the channel defined by the second tube.

34. The method of claim 33, wherein the diverter is configured to cooperate with the second tube to form a Y-arrangement or a T-arrangement.

35. The method of claim 33, wherein each diversion member includes a proximal end engaged with the distal end of the second tube, and an opposing distal end, and wherein the tubular member is configured to only allow flow of the aqueous humor outwardly of the distal end thereof from the cavity.

36. The method of claim 35, wherein one of the diversion members is configured to allow an inflow from the distal end thereof, wherein the inflow into the one of the diversion members is used to flush out the diversion members, without the inflow entering the distal end of the channel defined by the second tube.

37. The method of claim 20, comprising coating an external portion of the second tube for increasing patient comfort.

38. The method of claim 20, wherein at least a portion of the second tube is configured to extend through the conjunctival layer upon implantation of the apparatus, and the method comprises coating the at least a portion of the second tube with a porous cellular ingrowth material or forming the at least a portion of the second tube with the porous cellular ingrowth material.

* * * * *